United States Patent
Koga et al.

[11] Patent Number: 5,916,761
[45] Date of Patent: Jun. 29, 1999

[54] METHOD FOR ASSAYING VITAL SAMPLE

[75] Inventors: Shinji Koga; Shinichi Sakasegawa, both of Shizuoka, Japan

[73] Assignee: Asahi Kasei Kogyo Kabushiki Kaisha, Osaka, Japan

[21] Appl. No.: 09/077,390

[22] PCT Filed: Dec. 6, 1996

[86] PCT No.: PCT/JP96/03577

§ 371 Date: Jul. 28, 1998

§ 102(e) Date: Jul. 28, 1998

[87] PCT Pub. No.: WO97/24456

PCT Pub. Date: Jul. 10, 1997

[30] Foreign Application Priority Data

Dec. 27, 1995 [JP] Japan ................................ 7-340482
Feb. 19, 1996 [JP] Japan ................................ 8-030352

[51] Int. Cl.[6] .............................. C12Q 1/42; C12Q 1/48; C12Q 1/34
[52] U.S. Cl. .................. 435/21; 435/15; 435/17; 435/18; 435/19; 435/23; 435/24
[58] Field of Search ................ 435/21, 15, 17, 435/18, 19, 23, 24

[56] References Cited

U.S. PATENT DOCUMENTS 4,584,272  4/1986  Imahori et al. ..................... 435/21
5,250,416  10/1993  Ohno et al. ........................ 435/15

FOREIGN PATENT DOCUMENTS 9400836  1/1996  Netherlands .

OTHER PUBLICATIONS by W.M. Kengen et al., "Purification and Characterization of a Novel ADP–dependent Glucokinase from the Hyperthermophilic Archaeon Pyrococcus feriosus", *The Journal of Biological Chemistry*, vol. 270, No. 51, Dec. 22, 1995, pp. 30453–30457.

by W.M. Kengen et al., "Evidence for the Operation of a Novel Embden–Meyerhof Pathway That Involves ADP–dependent Kinases during Sugar Fermentation by Pyrococcus furiosus", *The Journal of Biological Chemistry*, vol. 269, No. 26, Jul. 1, 1994, pp. 17537–17541.

*Primary Examiner*—Louise N. Leary
*Attorney, Agent, or Firm*—Young & Thompson

[57] ABSTRACT

A method for determining adenosine 5' diphosphate (ADP) contained in a liquid sample by means of an enzymatic reaction, comprising reacting the sample at 15 to 45° C. at least in the presence of glucose, ADP-dependent hexokinase, and oxidized NAD(P), a glucose-6-phosphate dehydrogenase, and one or more salts releasing ions selected among magnesium, cobalt, and manganese ions and then determining the ADP contained in the sample together with the AMP resulting from the reaction based on the amount of the reduced NAD(P) yielded. This method has advantages in that the limit of determination is high because ADP is determined based on the amount of the reduced NAD(P) yielded, and since the reduced NAD(P) has a definite molecular extinction coefficient, the value found is highly reliable and uninfluenced by the reducing substances contained in the sample.

20 Claims, 17 Drawing Sheets

METHOD FOR ASSAYING VITAL SAMPLE

FIELD OF THE INVENTION

This invention relates to a method for determining adenosine 5' diphosphate ADP contained in a liquid sample by means of an enzymatic reaction, which comprises reacting the sample at 15 to 45° C. at least in the presence of glucose, ADP-dependent hexokinase (ADP-HK), oxidized NAD(P) [oxidized nicotinamide adenine dinucleotide (phosphate)], glucose-6-phosphate dehydrogenase (G6PDH), and one or more ion releasing salt selected from the group consisting of magnesium, cobalt and manganese ions and determining the ADP contained in the sample together with the AMP resulting from the reaction based on the amount of the reduced NAD (P) [reduced nicotinamide adenine dinucleotide (phosphate)] yielded. The present invention further relates to a method for determining an enzyme for generating ADP or substrate thereof in a liquid sample by means of an enzymatic reaction, which comprises reacting the sample containing the enzyme for generating ADP or substrate thereof in the liquid sample at 15 to 45° C. at least in the presence of a reaction reagent involving in the reaction based on the enzyme for generating ADP and the substrate thereof,ATP, glucose,ADP-HK, oxidized NAD (P), G6PDH and one or more ion releasing salt of magnesium ion, cobalt ion or manganese ion, and determining the enzyme for generating ADP or the substrate thereof contained in the sample together with the AMP resulting from the reaction based on the amount of the reduced NAD (P) yielded. The invention is applicable in the clinical chemistry. The method has advantageous for sample and exact assay of the ADP in the sample such as serum, plasma, urine and cerebrospinal fluid, by means of an amount of generation of or increase in the reduced NAD (P).

PRIOR ARTS

Methods for asssaying ADP in biological sample or enzyme, which generate ADP, or substrate thereof have known. These include a method using combination of the enzyme and other dehydrogenase or oxidase for the reaction product from substrate and the enzyme (for example, in case of enzymatic reaction with glycerol and glycerokinase, a method wherein glycerokinase is reacted with glycerol in the presence of ATP to generate ADP and glycerol phosphate, which is assayed by an action of glycerol phosphate dehydrogenase or glycerol phosphate oxidase) and a method assyaing ADP which is generated by enzymatic action.

However, in the method of assay by combining with other dehydrogenase or oxidase, a combination of each enzyme should be changed depending on the enzyme for generating ADP. This is not suitable for general use, furthermore there are possibilities of no enzymes with preferable combination for substrate or enzyme.

A method for assaying ADP,which is generated by enzymatic reaction, includes an assay by means of liquid chromatography. This has disadvantage due to complicated chromatographic operation.

Enzymatic assay methods of ADP which has good operability have known (Japan. Pta. Unexam. Publ. 7-8297). These include : a method measuring decreased reduced NAD (NADH+H$^{30}$) using pyruvate kinase [PK (EC 2. 7. 1. 40)] and lactate dehydrogenase [LDH (EC 1. 2. 3. 3)] (decreased method, Reaction 1); a method using pyruvate kinase and pyruvate oxidase (oxidasemethod, Reaction 2); and a method measuring increase reduced NAD (P)[NAD (P) H+H$^{30}$] using pyruvate kinase, pyruvate decarboxylase and aldehyde dehydrogenase (increased method, Reaction 3).

The reactions of these methods are shown below.

In the equation ; PEP: phosphoenolpyruvate. Pi: phosphate, PDC: pyruvate decarboxylase, A1DH: aldehyde dehydrogenase, ans TPP: thiamine pyrophosphate.

(Reaction 1)

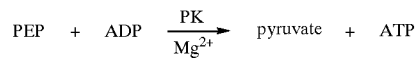

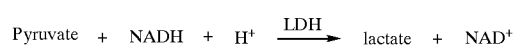

(Reaction 2)

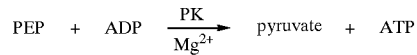

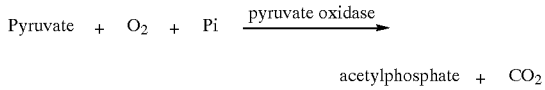

(Reaction 3)

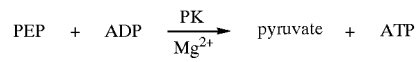

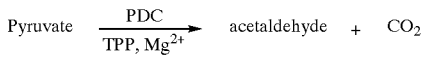

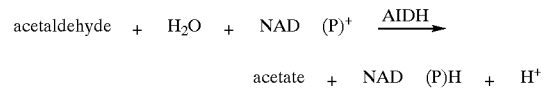

In the decreased method of reduced NAD (NADH+H$^{30}$) shown in Reaction 1, previously alliquot amount of reduced NAD should be added in the reaction mixture, and after termination of the reaction, residual amount of reduced NAD in the reaction mixture is measured. Consequently, this decreased method has number of problems as follows.

(1) Assay value is not exact in case of small amount of components for assay.
(2) Uper limit of an amount of measurable components is restricted by an amount of added reduced NAD in the reaction mixture.
(3) Amount of addition of the reduced NAD in the reaction mixture before assay should be controlled depending on the type of spectrophotometer for measurement of reduced NAD.
(4) Reduced NAD in the reagent for analysis is unstable.

Quantitative assay of pyruvate by means of coloring indicator reagent of hydrogen peroxide, which is generated from the reaction by using pyruvate kinase and pyruvate as shown in Reaction 2, has known.

(5) The method is affected by an interfering substance (reduced substance) (such as uric acid and ascorbate) or color substance (bilirubin, hemoglobin, etc.) in the biological samples. Consequently, result of assay is not so exact and is not satisfactory, As shown in the reaction 3, the increased method of reduced NAD (P) using pyruvate kinase, pyruvate decarboxylase and aldehyde dehydrogenase is used to apply the reverse reaction of pyruvate kinase.

(6) Optimum pH of the reverse reaction is pH 7.5. Optimum pH of pyruvate decarboxylase is pH 6.0–6.4 and that of aldehyde dehydrogenase is pH 9.0. Optimum pH of these enzymes is different. This resulted to determine optimum pH of the reaction 3.
(7) Since Km value of pyruvate decarboxylase for pyruvate is slightly hight as 3.6–30 mM, large amount of substrate, which is also expensive, should be used for generating pyruvate.

(8) Large amount of enzyme is required for shortage of the reaction time. These result indicates that the method of the reaction 3 makes to complicate for operation.

Intracellular ADP dependent hexokinase, which may be used in the present invention, in super thermophile pyrococcus furiosus DSM 3638 has known [J. Biol. Chem., 269, 17537–17541, (1994), Dutch Patent Open No. 9400 836]. However, no physicochemical and biochemical properties is reported. Moreover the enzyme is neither isolated nor purified. Furthermore growth temperature of the microorganism strain is 90° C.–105° C. Since the optimum pH of the enzyme is above 90° C., assay of enzyme activity is performed at 50° C. for considering heat stability of G6PDH, which is originated from yeast. This indicates that the assay of enzyme action is performed in the different optimum temperature of ADP-HK, and the reaction condition is completely different from the assay condition of general clinical diagonosis for analysis of biological specimens in view of the optimum temperature of ADP-HK.

(6) If the reaction as like, in this prior reference, is performed at 50° C., it is not preferable in the clinical chemistry for exact assay due to denature of the combination of the enzymes.

(7) Turbidity of the reaction mixture occurs due to thermal denaturation of the biological components.

As a result, these prior art methods have number of problems and the exact assay is impossible.

Problems to be Solved by the Invention

We have cultured a strain of Pyrococcus furiosus DSM3638, purified ADK-HK, measured its optimum temperature and determined to 80° C.–100° C. Further, we have found that relative activity of the enzyme at 37° C. was about 10% as cpmpared to at 100° C. Consequently, it has been considered that the exact enzyme reaction at 37° C. using the enzyme might be impossible. However, quite unexpectedly, as a result of the enzyme reaction at 37° C., we have found that ADP in the specimen such as biological composition could exctly and simply be assayed as an increased amount and generation of reduced NAD (P) at 15° C.–45° C., which included the experimented temperature at 37° C. with a general reaction temperature for determination of biological sample.

We have found a method for assaying the ADP in a biological sample, or the enzyme which generated ADP in the biolopgical sample or its substrate by using the enzymatic reaction hereinbelow illustrated (Reactions 4 and 5). For example, in case that the biological sample is a liquid specimen for assaying enzymatic activity, which generates ADP, reaction reagents, which involve in the reaction including ADP generating enzyme and its substrate, are used in the presence of the substrate of the enzyme and the ATP, or in case that the biological sample is a liquid specimen for an assay of amount of substrate, reaction reagents, which involve in the reaction including ADP generating enzyme and its substrate, are used in the presence of the enzyme, which generate ADP by a reaction with the substrate, and ATP. The said liquid specimen is treated with the said reaction reagents. The reaction proceeds based on a reaction involving in glucose, ADP-HK, oxidized NAD (P), G6PDH and magnesium ion cobalt ion or manganese ion, to generate AMP from ADP, simultaneously to generate reduced NAD (P) by a reducing reaction of the oxidized NAD (P). We have found that the quantitative assay of ADP generating enzyme or its sybstrate in the biological sample based on the assay of the generated reduced NAD (P) was quite useful, and that these enzymatic reaction could be applied generally to the enzyme, which generate ADP, or its substrate in the biological sample, and completed the present invention.

An object of the present invention is to provide a method for assaying ADP in a biological sample comprising measuring the said ADP as a generated and increased amount of reduced NAD (P) by using glucose, ADP-HK, oxidized NAD (P), G6PDH and magnesium ion, conbalt ion or manganese ion.

Another object of the present invention is to provide a method for simple and precise assay of an enzyme, which generates ADP, or its substrate in a biological sample to be assayed, comprising using reaction reagents which involve in a reaction beased on the enzyme, which generates ADP, and its substrate, and reacting the ADP generating enzyme and substrate thereof in the presense of ATP, glucose, ADP-HK, oxidized NAD (P), G6PDH and magnesium ion, cobalt ion or manganese ion.

Means for Solving the Problems

The present invention has been completed by the knowledge hereinabove. The present invention relates to a method for determining ADP contained in a liquid sample by means of an enzymatic reaction, which comprises reacting the sample at 15 to 45° C. at least in the presence of glucose, ADP-HK, oxidized NAD (P), G6PDH and one or more ion releasing salt selected from the group consisting of magnesium, cobalt and manganese ions, and determining the ADP contained in the sample together with the AMP resulting from the reaction based on the amount of the reduced NAD (P) yielded. The present invention further relates to a method for determining an enzyme for generating ADP or substrat thereof in a liquid sample by means of an enzymatic reaction, which comprises reacting the sample containing the enzyme for generating ADP or substrate thereof in the liquid sample at 15 to 45° C. at least in the presence of a reaction reagent involving in the reaction based on the enzyme for generating ADP and the substrate thereof, ATP, glucose, ADP-HK, oxidized NAD (P), G6PDH and one or more ion releasing salt of magnesium ion, cobalt ion or manganese ion, and determining the enzyme for generating ADP or the substrate thereof contained in the sample together with the AMP resulting from the reaction based on the amount of the reduced NAD (P) yielded.

The enzymatic reactions, which generate the reduced NAD (P) from the oxidized NAD (P) in the presence of glucose, ADP-HK, oxidized NAD (P), G6PDH and one or more ion releasing salt selected from the group consisting of magnesium, cobalt and manganese ions used in the present invention, are shown in the following Reactions 4 and 5.

(Reaction 4)

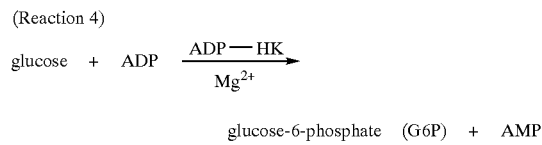

glucose + ADP $\xrightarrow[\text{Mg}^{2+}]{\text{ADP}-\text{HK}}$ glucose-6-phosphate (G6P) + AMP (Reaction 5)

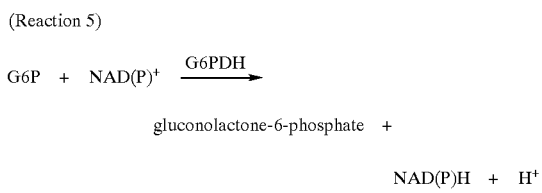

G6P + NAD(P)$^+$ $\xrightarrow{\text{G6PDH}}$ gluconolactone-6-phosphate + NAD(P)H + H$^+$ The present invention will be explained in details as follows.

ADP-HK of the prenent invention is an enzyme ADP-HK which uses at least glucose as a substrate and consumes ADP to generate glucose-6-phosphate and AMP as shown in the above Reaction 4, and is not limited thereto. Example of ADP-HK producing microorganism is a super thermophile pyrococcus furiosus DSM3638, which has deposited in Deutsche Sammlung von Mikroorganismen und Zellkulturen GmbH (DSM) and mentioned in the DSM catalogue (1993), and can be obtainable by any person. The super thermophile ADP-HK is a preferable example of the enzyme.

G6PDH used in the enzymatic reaction of the above Reaction 5 is distributed in the market (Boehringer Mannheim Inc: Leuconostoc mesenteroides, Sigma Corp: Baker's yeast, Bacillus strearothermophilus and Leuconostoc mesenteroides), and is easily obtainable.

In the Reaction 4, the enzymatic reaction catalyzed by ADP-HK, the ion releaasing salt of magnesium ion can be replaced by one or more ion releasing salt of cobalt or manganese. Example of the salt includes chloride or sulfate, and is preferably magnesium chloride, cobalt chloride or manganese chloride, but is not limited to these examples.

Oxidized NAD (P), which is a coenzyme used in the enzymatic reaction by the above G6PDH, as exemplified in Reaction 5, includes oxidized thio-NAD (P), oxidized 3-acetyl NAD (P) and oxidized deamino NAD (P), but is not limited within these examples.

In the present invention, the amount of ADP-HK, G6PDH, glucose, oxidized NAD (P) and magnesium ion, cobalt ion or manganese ion used can be the amount for good process of the enzymatic reaction. It can be adjusted depending on the types of substance in the specimen to be assayed, contents in the specimen, types of coupling enzymatic reaction, reaction time and temperature. Examples of concentration of ADP-HK and G6PDH are 0.1–100 U/ml, preferably 1–50 U/ml. Concentration of glucose and oxidized NAD (P) can be sufficient level for enzymatic reaction. Example of glucose concentration is 0.5–100 mM, preferably 1–50 mM. Example of oxidized NAD (P) concentration is 0.5–50 mM, preferably 1–10 mM. Example of magnesium ion, cobalt ion or manganese ion is 0.1–50 mM, preferably 0.5–10 mM.

The method of the present invention proceeds with using preferable buffer solution which does not show detrimental action to the enzymatic reaction. Example thereof is Tris-HCl buffer solution, phosphate buffer solution, mono- or di-ethanolamine buffer solution or Good's buffer solution. Assay procedures are not limited. Examples thereof are end-point asay method and rate assay method. Examples of sample solution to be assayed are biological sample which contains ADP (existed or generated), and are specimens such as serum, plasma, urine and cerebrospinal fluid. The specimen used in the assay may be 5–200 μl. Reaction temperature can be proceeded at 15–45° C., preferably at 20° C.–40° C. The reaction time in the end point assay is 1–60 min., preferably 1–10 min. In the rate assay method, the measurement is performed within a time for linear reaction, preferably in the interval of 2–3 min.

In the reaction of the present invention, ADP in the specimen is converted to AMP which is accompanied by generation of the reduced NAD (P). The reduced NAD (P) can be assayed by various methods, usually optical absorption, which is prefereably for simple and precise measurement. Wave length for measurement can be selected depending on the type of reduced NAD (P). Reduced NAD (P), reduced 3-acetyl-NAD (P) and reduced deamino-NAD (P) can be measured at 340 nm, and reduced thio-NAD (P) is measured at 405 nm. Another method for measurement of the reduced NAD (P) includes that formazan is generated by an action of electro acceptor such as phenazine methosulfate (PMS) or diaphorase (EC 1. 6. 4. 3) by using tetrazorium salt such as indonitro tetrazorium (INT) or nitroblue tetrazorium (NTB), and the said formazan is colorimetrically measured. Reduced NAD (P) is also measured by fluorometry.

The specimen as a biological sample of the present invention is used for assay of ADP in the biological sample, or assay of substrate for enzyme which generates ADP in the biological sample or assay of the enzyme activity in the biological sample. In the assay of substrate for an enzyme which genenrate ADP in the biological sample or the assay of the enzyme activity, especially in the assay of the enzyme which genenrates ADP or the substrate thereof in the presence of ATP, the substrate of kinase, synthetase, hydratase or carboxylase in the specimen can be converted to ADP by an action of kinase, synthetase, hydratase or carboxylase. Accordingly, the enzyme activity or substrate thereof, which is introduced to ADP, in the specimen can be assayed as a generated amount of the reduced NAD (P) by coupling with these enzyme reactions and the enzyme reaction of Reactions 4 and 5. In Table 1, examples of substrates and enzyme used are shown. Either the substrate or the enzyme activity can be measured by using either the enzyme or the substrate as a reaction reagent (ATP is not an objective for the assay).

TABLE 1

| Reaction No. | Substrate | Enzyme |
| --- | --- | --- |
| 6 | urea | urea amidohydrolase (EC 3. 5. 1. 45) |
| 7 | creatinine | creatinine amidohydrolase (EC 3. 5. 2. 10) creatine kinase (EC 2. 7. 3. 2) creatine amidohydrolase (EC 3. 5. 3. 3) urea amidohydrolase (EC 3. 5. 1. 45) |
| 8 | creatinine | creatinine deiminase (EC 3. 5. 4. 21) N-methylhydantoinase (EC 3. 5. 2. 14) |
| 9 | creatine | creatine kinase (EC 2. 7. 3. 2) |
| 10 | glycerol | glycerol kinase (EC 2. 7. 1. 30) |
| 11 | choline | choline kinase (EC 2. 7. 1. 32) |
| 12 | hexose | hexokinase (EC 2. 7. 1. 1) |
| 13 | fructose | fructokinase (EC 2. 7. 1. 4) |
| 14 | galactose | galactokinase (EC 2. 7. 1. 6) |
| 15 | glucosamine | glucosamine kinase (EC 2. 7. 1. 8) |
| 16 | adenosine | adenosine kinase (EC 2. 7. 1. 20) |
| 17 | thymidine | thymidine kinase (EC 2. 7. 1. 21) |
| 18 | NAD | NAD kinase (EC 2. 7. 1. 23) |
| 19 | riboflavin | riboflavin kinase (EC 2. 7. 1. 26) |
| 20 | pyridoxal | pyridoxal kinase (EC 2. 7. 1. 35) |
| 21 | mevalonate | mevalonate kinase (EC 2. 7. 1. 36) |
| 22 | protein | protein kinase (EC 2. 7. 1. 37) |
| 23 | homoserine | homoserine kinase (EC 2. 7. 1. 39) |
| 24 | pyruvate | pyruvate kinase (EC 2. 7. 1. 40) |
| 25 | pyruvate | pyruvate carboxylase (EC 6. 4. 1. 1) |

TABLE 1-continued

| Reaction No. | Substrate | Enzyme |
|---|---|---|
| 26 | acetate | acetate kinase (EC 2. 7. 2. 1) |
| 27 | ammonia | carbamate kinase (EC 2. 7. 2. 2) |
| 28 | L-arginine | arginine kinase (EC 2. 7. 3. 3) |
| 29 | L-glutamate ammonia | glutamine synthetase (EC 6. 3. 1. 2) |
| 30 | L-glutamate | glutamate kinase (EC 2. 7. 2. 11) |
| 31 | L-aspartate ammonia | aspartate synthetase (EC 6. 3. 1. 4) |
| 32 | L-aspartate | aspartate kinase (EC 2. 7. 2. 4) |
| 33 | ATP | myokinase (EC 2. 7. 4. 3) |
| 34 | ATP | ATPase (EC 3. 6. 1. 4) |
| 35 | citrate | citrate kinase (EC 4. 1. 3. 8) |
| 36 | L-aspartate | aspartate aminotransferase(GOT) (EC 2. 6. 1. 1) glutamine synthetase (EC 6. 3. 1. 2) |
| 37 | L-alanine α-ketoglutarate | alanine aminotransferase (GPT) (EC 2. 6. 1. 2) glutamine synthetase (EC 6. 3. 1. 2) |

These reactions are illustrated as follows.

In the asasy of urea or urea amidohydrolase in the specimen, a reaction using the reaction reagents involved in the reaction is illustrated in the following. In this assay, ADP, which is generated by the enzymatic reaction, is measured. The reaction reagents involved in the reaction mean the components shown in the left part of the reaction scheme and in the part of arrow. The reaction reagents in an assay of urea in the biological sample include urea amidohydrolase, water, magnesium ion (magnesium chloride) and potassium hydrogen carbonate. The reaction reagents in an assay of urea amidohydrolase activity in the biological sample include urea, water, magnesium ion (magnesium chloride) and potassium hydrogen carbonate. In these reactions, water is replaced by water in the reaction medium.

(Reaction 6) urea amidohydrolase

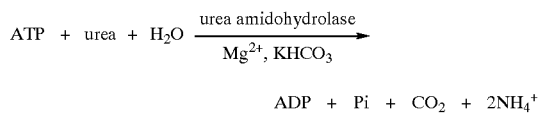

$$ATP + urea + H_2O \xrightarrow[Mg^{2+}, KHCO_3]{urea\ amidohydrolase} ADP + Pi + CO_2 + 2NH_4^+$$

In the assay of creatinine or creatinine amidohydrolase in the biological sample, the reactions using the reaction reagents involved in the reactions are illustrated in the following. In such the consecutive enzymatic reactions, in case that a component in the left side of the reaction is identical with that in the right side of the reaction, those components are involved in the reaction, but those are apparently not necessary to be added.

In the reaction 1̂ and 2̂ hereinbelow illustrated, and in the assay of creatinine or creatinine amidohydrolase in the biological sample creatine, which is generated by an enzymatic reaction, can be assayed by measuring ADP generated in the reaction 1̂ or in the reaction 2̂.

In an assay of creatinine in the biological sample, the reaction reagents involved in the reaction are creatinine amidohydrolase, water, creatine kinase (CK) and magnesium ion for the reaction 1̂, or creatinine amidohydrolase, water, creatine amidohydrolase, urea, ureido amidohydrolase and magnesium ion for the reaction 2̂.

(Reaction 7) creatinine, creatinine amidohydrolase

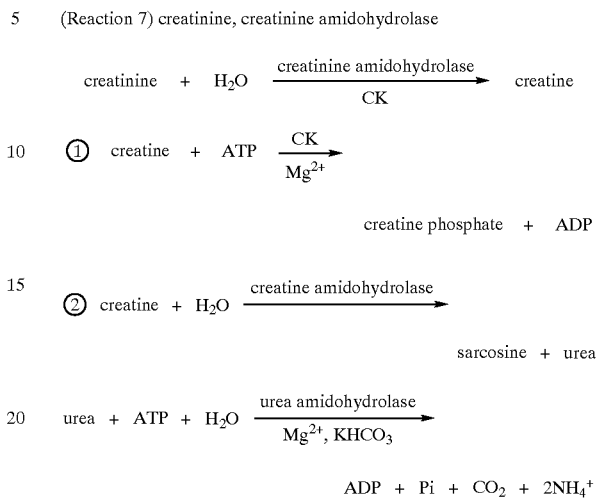

In the assay of creatinine or creatinine deiminase in the biological sample, the reaction using the reaction reagents involved in the reactions are illustrated in the following. In this reaction, ADP generated by an action of enzyme is measured. The reaction reagents for assay of creatinine in the biological sample are creatinine deiminase, water and N-methylhydantoinase. The reaction reagents for assay of creatinine deiminase activity in the biological sample are creatinine, water and N-methylhydantoinase.

(Reaction 8) creatinine, creatinine deiminase

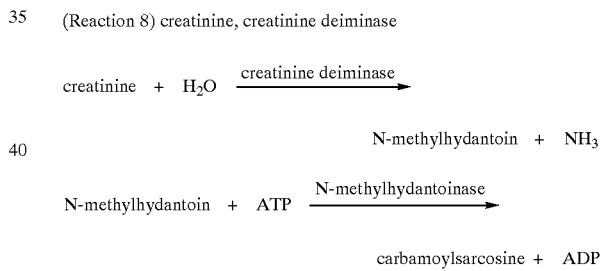

In the assay of creatine or kinase in the biological sample, the reaction using the reaction reagent involved in the reaction is illustrated in the following. In this reaction, ADP, which is generated by the enzymatic reaction, is measured. The reaction reagents used for assaying creatine are creatine kinase and magnesium ion. The reaction reagnets used for assay of creatine kinase activity in the biological sample are creatine and magnesium ion.

(Reaction 9) creatine, creatine kinase

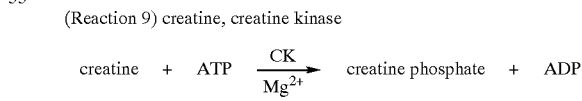

Creatine in the reaction 9 can be the creatine generated in the above reaction 7.

In the assay of glycerol or glycerol kinase (GK) in the biological sample, the reaction scheme is shown in the following, and generated ADP by the enzymatic action is measured. In the reaction, the reagents used are glycerol kinase and magnesium ion.

(Reaction 10) glycerol, glycerokinase

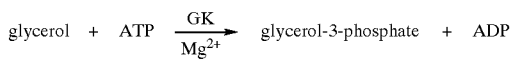

Glycerol in the above reaction can be the glycerol liberated from triglyceride or mono- or di-glyceride by an action of lipase or pancreatic lipase, to which activating agent Co-lipase is added, or the glycerol liberated from phosphatidylglycerol by an action of phospholipase D.

The reaction is preferable for assay of triglyceride and assay of pancreatic lipase activity using synthetic substrate of triglyceride or diglyceride in the biochemical test of the specimen.

For example, the reagents used for an assay of triglyceride in the biological sample are lipase, water, glycerol kinase and magnesium ion. The reagents used for assaying pancreatic lipase are synthetic substrate such as triglyceride or diglyceride, water, glycerol kinase, magnesium ion, Co-lipase and surface active agent for solvilizing the synthetic substrate.

In the assay of choline or choline kinase, the reaction scheme is shown in the following. In this reaction, enzymatically generated ADP can be measured.

(Reaction 11) choline, choline kinase

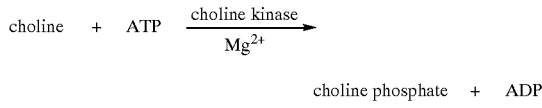

Choline in the reaction may be a liberated choline from phosphatidylcholine (component of phospholipid) by an action of phospholipase D, and from synthetic substrate of choline ester such as benzoil choline or o-toluoylcholine by an action of choline esterase.

The method is preferable for assay of choline esterase activity in an assay of phospholipid component in the biochemical test using synthetic substrate.

The reaction reagents used for the assay of phospholipid component are phospholipase D, water and magnesium ion, and the reagents used for the assay of choline esterase activity are synthetic substrate such as benzoyl choline or o-tolyoylcholine, water and magnesium ion.

In the assay of substrate or enzyme which generate ADP in the biological sample, the reaction schemes, in which the components involved in the said reaction are used as the reaction reagents, is illustrated in the following. In these reaction, ADP generated by the enzymatic reaction can be measured.

In the assay method of the present invention, the reaction reagents of the components involved in the reaction of the present invention are obvious in view of the above and below illustrated reaction schemes.

Further, these can preferably be prepared optionally depending on the sample to be assayed, and are not limited to the reagents described in the specification.

(Reaction 12) hexose, hexokinase

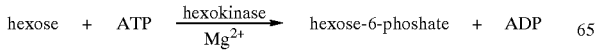

(Reaction 13) fructose, fructokinase

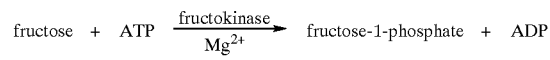

(Reaction 14) galactose, galactokinase

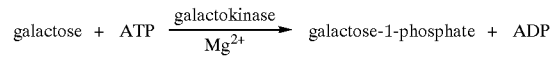

(Reaction 15) glucosamine, glucosamine kinase

(Reaction 16) adenosine, adenosine kinase

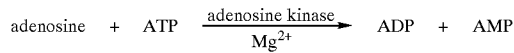

(Reaction 17) thymidine, thymidine kinase

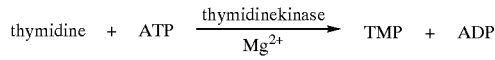

(Reaction 18) NAD, NAD kinase

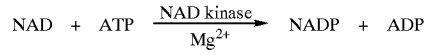

(Reaction 19) riboflavin, riboflavin kinase

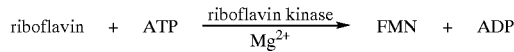

(Reaction 20) pyridoxal, pyridoxal kinase

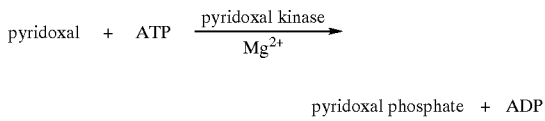

(Reaction 21) mevalonate, mevalonate kinase

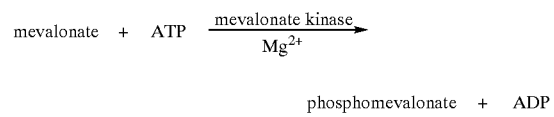

(Reaction 22) protein, protein kinase

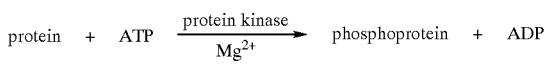

(Reaction 23) homoserine, homoserine kinase

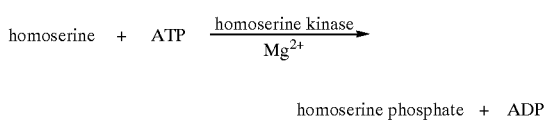

-continued (Reaction 24) pyruvate, pyruvate kinase

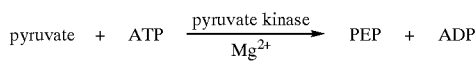

(Reaction 25) pyruvate, pyruvate carboxylase

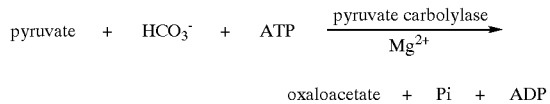

(Reaction 26) acetate, acetate kinase

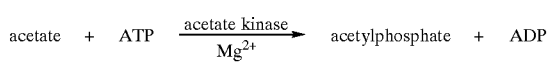

(Reaction 27) ammonia, carbamine kinase

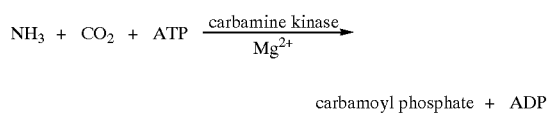

(Reaction 28) L-arginine, argine kinase

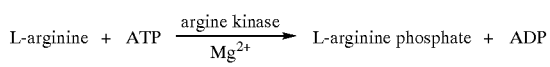

(Reaction 29) L-glutamate, ammonia, glutamine synthetase

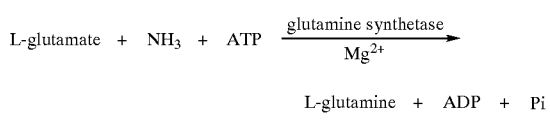

In the above reaction, ammonia to be assayed can be generated by a reaction with urea and urea amidohydrolase as illustrated in the Reaction 6, or by a reaction with creatinine and creatinine amidohydrolase as illustrated in the reaction 2̂ of the Reaction 7, or by a previous step of the reaction with creatinine and creatinine deiminase as illustrated in the Reaction 8. Ammonia in these reactions is not limited in its origin.

(Reaction 30) L-glutamate, glutamate kinase

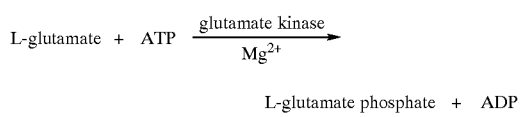

(Reaction 31) L-aspartate, ammonia, aspargine synthetase

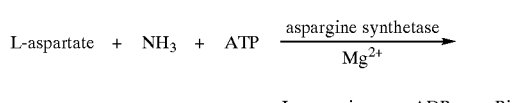

(Reaction 32) L-aspartate, L-aspartate kinase

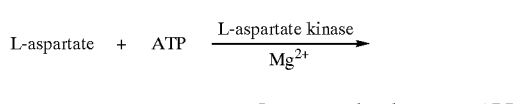

-continued (Reaction 33) ATP, myokinase

(Reaction 34) ATP, ATPase

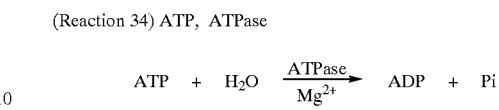

(Reaction 35) citrate, citrate kinase

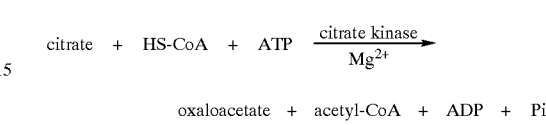

(Reaction 36)
L-aspartate, α-ketoglutarate, aspartate aminotransferase (GOT)

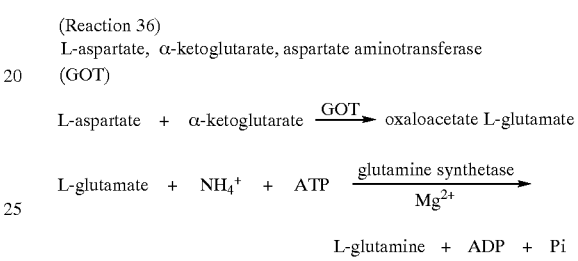

The above reaction is preferably used in an assay of GOT activity.

(Reaction 37) L-alanine, α-ketoglutarate, alanine aminotransferase (GPT)

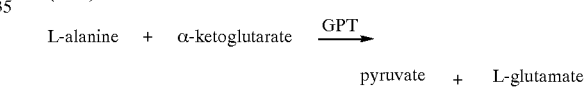
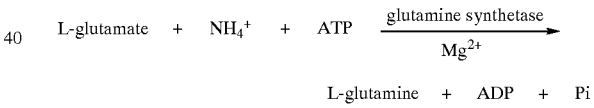

The above reaction is preferable for use of an assay of an assay of GPT activity.

In these reactions, amount of ATP added is for example 0.1–50 mM, preferably 0.5–10 mM. Enzyme added for an assay of substrate is, for example, 1–100 U/ml. Substrate to be added in an assay of enzyme activity is, for example 1–100 mM. In the reagents other than these substrates and enzyme, components which are consumed by reaction with the substrate are equal to 2-fold of the amount of the above substrates used. Concentration of magnesium ion is, for example, 0.1–50 mM as magnesium chloride, preferably 0.5–10 mM, however excess use is not excluded unless inhibition in the reaction occurs.

These reaction may be coupled with the Reactions 4 and 5 or may not be coupled. Preferable reaction proceed in couple of these reactions.

In the prior known assay method of urea, reaction proceeds accroding to the Reaction 38 as follows.

(Reaction 38)

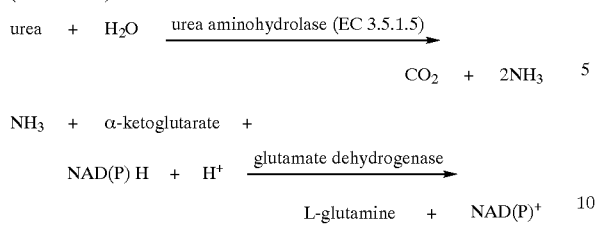

As shown in Reaction 38, the method includes measurement of decreased amount of reuduced NAD (P). In this reaction, there are many disadvantages as follows.
(8) Assay result may be incorrect in case of small amount of components to be assayed.
(9) The upper limit of measurable components is restricted depending upon the added reduced NAD (P) in the reaction (narrow range of the measurement).
(10) Amount of reduced NAD (P) in the reaction mixture before assay should be changed depending on the type of spectrophotometer which is used for measurement of the reduced NAD (P).
(11) Reduced NAD (P) in the reagent is unstable.
(12) Application to dry chemistry is impossible.
(13) The reaction consists of a method for measurement of ammonium in its principle, and ammonia in the specimen or reagents must be removed previously.

The assay method of the present invention is:

(Reaction 39)

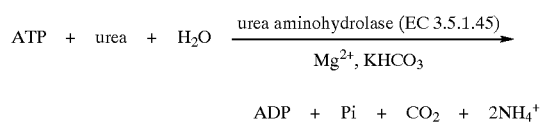

(Reaction 40)

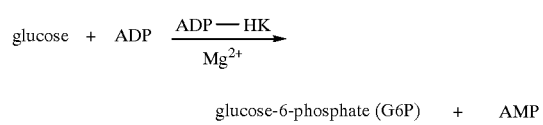

(Reaction 41)

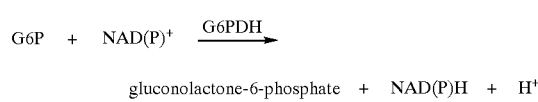

As shown in the above reactions 39, 40 and 41, since the reaction is the increased method of reduced NAD (P), there are no disadvantages of the decreased method as well as no need for removal of ammonia. Therefore the present method is superior.

Prior known conventional assay method of creatine kinase is illustrated as follows.

(Reaction 42)

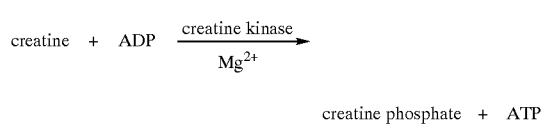

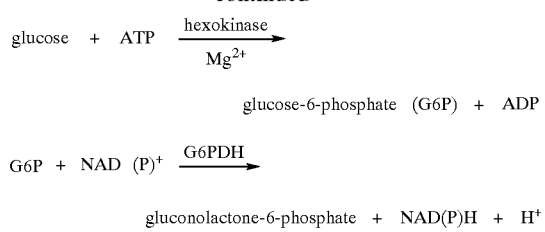

In this reaction system, a substrate creatine phosphate is quite expensive which leads to expensive reagents in total.

The method of the present invention can be illustrated as follows.

(Reaction 43)

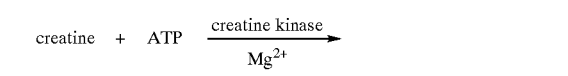

(Reaction 44)

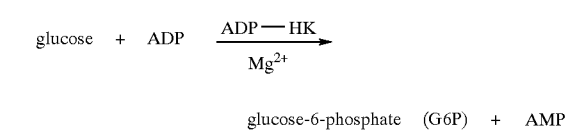

(Reaction 45)

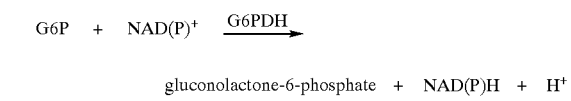

As shown in the reactions 43, 44 and 45, creatine is used as substrate which results to provide reagents for assay with low price.

Conventional known method for creatinine assay is illustrated as follows.

(Reaction 46)

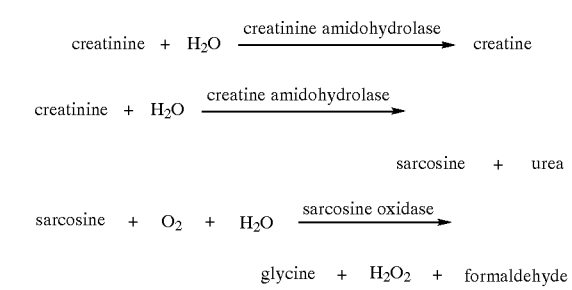

As shown in the above reaction scheme 46, the assay involves in oxidase method. The reaction is affected by the reducing substance (ascorbate) to result unexpect assay. Further, sarcosine oxidase reacts with proline in a sample, consequently the reaction is affected by proline in the specimen.

The methods of the present invention can be illustrated as follows.

(Reaction 47)

creatinine + H₂O —creatinine amidohydrolase→ creatine creatine + ATP —creatine kinase→ creatine phosphate + ADP (Reaction 48)

glucose + ADP —ADP-HK / Mg²⁺→ glucose-6-phosphate (G6P) + AMP (Reaction 49)

G6P + NAD(P)⁺ —G6PDH→ gluconolactone-6-phosphate + NAD(P)H + H⁺

(Reaction 50)

creatinine + H₂O —creatinine deiminase→ N-methylhydantoin + NH₃

N-methylhydantoin + ATP + H₂O —N-methylhydantoinase→ carbamoylsarcosine + ADP (Reaction 51)

glucose + ADP —ADP-HK / Mg²⁺→ glucose-6-phosphate (G6P) + AMP (Reaction 52)

G6P + NAD(P)⁺ —G6PDH→ gluconolactone-6-phosphate + NAD(P)H + H⁺

As shown in the reactions 47, 48 and 49, and the reactions 50, 51 and 52, these are increased method of the reduced NAD (P). The reactions are not affected by the reducing substance (ascorbate) and proline.

Consequently assay method of triglyceride is shown as follows.

(Reaction 53)

triglyceride + 3H₂O —lipase→ glycerol + 3 fatty acids glycerol + ATP —glycerol kinase / Mg²⁺→ glycerol phosphate + ADP glycerol phosphate + O₂ + H₂O —glycero phosphate oxidase→ dihydroxyacetone phosphate + H₂O As shown in the above reaction scheme 53, the reaction consists of the oxidase method, which is affected by reducing substance (ascorbate) in the specimen and result of assay may be inexact.

The method of the present invention is illustrated by the following reactions.

(Reaction 54)

triglyceride + 3H₂O —lipase→ glycerol + 3 fatty acids glycerol + ATP —glycerol kinase / Mg²⁺→ glycerol phosphate + ADP (Reaction 55)

glucose + ADP —ADP-HK / Mg²⁺→ glucose-6-phosphate (G6P) + AMP (Reaction 56)

G6P + NAD (P)⁺ —G6PDH→ gluconolactone-6-phosphate + NAD(P)H + H⁺

As shown in the above reactions 54, 55 and 56, the method of the present invention is an increased method of reduced NAD (P) and is not influenced by the reducing substance in the specimen.

In replace of triglyceride of the above reaction 54 to diglyceride or monoglyceride, in which the reaction proceeds by consuming 2 moles or 1 mole of water to liberate 2 moles or 1 mole of fatty acid, the result is identical with the aboves.

Conventional assay method of phosphatidylcholine is illustrated as follows.

(Reaction 57)

phosphatidylcholine + H₂O —phospholipase D→ phosphatidate + choline choline + 2O₂ + H₂O —choline oxidase→ betaine + 2H₂O₂

As shown in the above reaction scheme 57, the method is the oxidase method, which is influenced by a reducing substance (ascorbate), and produces inexact result.

The method of the present invention is illustrated as follows.

(Reaction 58)

phosphatidycholine + H₂O —phospholipase D→ phosphatidate + choline choline + ATP —choline oxidase / Mg²⁺→ choline phosphate + ADP (Reaction 59)

glucose + ADP —ADP-HK / Mg²⁺→ glucose-6-phosphate(G6P) + AMP (Reaction 60)

gluconolactone-6-phosphate + NAD(P)H +H⁺

As shown in the reactions 58, 59 and 60, the method of the present invention is the increased NAD (P) method, which is not influenced by a reducing substance.

Conventional assay method of aspartate aminotransferase (GOT) is illustrated in the reaction 61.

(Reaction 61)

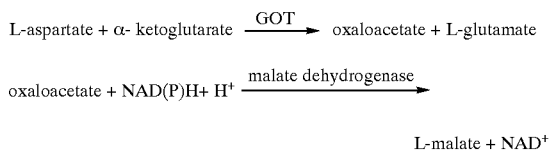

L-malate + NAD⁺

As shown in the reaction sheme 61, the method is the decreased method of NAD. The method has disadvantages as follows.
(14) Assay result is incorrect in case of small amount of components to be assayed.
(15) The upper limit of measurable components is restricted depending on the added reduced NAD in the reaction (narrow range of the measurement).
(16) Amount of reduced NAD in the reaction mixture before assay has to be changed depending on the type of spectrophotometer used for measurement of the reduced NAD.
(17) Reduced NAD in the reagent is unstable.
(18) Application to dry chemistry is impossible.

Further the method is influenced by lactate dehydrogenase in the specimen which indicate impossible to proceed exact assay.

The method of the present invention is shown as follows.

(Reaction 62)

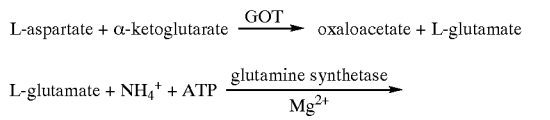

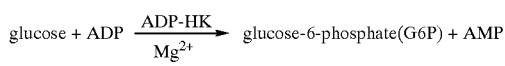

L-glutamine + ADP + Pi (Reaction 63)

glucose + ADP $\xrightarrow[\text{Mg}^{2+}]{\text{ADP-HK}}$ glucose-6-phosphate(G6P) + AMP (Reaction 64)

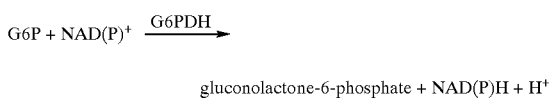

gluconolactone-6-phosphate + NAD(P)H + H⁺

As shown in the reactions 62, 63 and 64, the present method is the increased reduced NAD (P). The method has no disadvantages as like in the conventional reduced method. Furthermore, it needs not to remove lactate dehydrogenase in the specimen. As a result, the present method shows superior result.

Prior known conventional alanine aminotransferase (GPT) is illustrated as follows.

(Reaction 65)

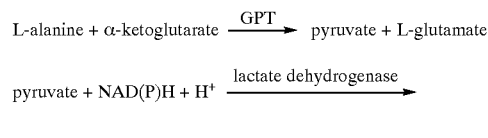

lactate + NAD⁺

As shown in the above reaction scheme 65, the method is the decreased method of NAD. The method has disadvantages as follows.
(19) Assay result is incorrect in case of small amount of components to be assayed.
(20) The upper limit of measurable components is restricted depending on the added reduced NAD in the reaction (narrow range of the measurement).
(21) Amount of reduced NAD in the reaction mixture before assay has to be changed depending on the type of spectrophotometer used for measurement of the reduced NAD.
(22) Reduced NAD in the reagent is unstable.
(23) Application to dry chemistry is impossible.

Further the method is influenced by lactate dehydrogenase in the specimen which indicates impossible to proceed exact assay.

The method of the present invention is shown as follows.

(Reaction 66)

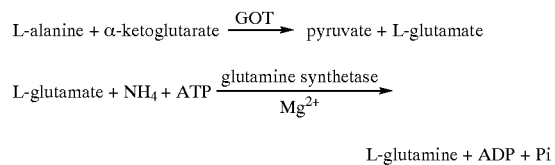

L-glutamine + ADP + Pi (Reaction 67)

glucose + ADP $\xrightarrow[\text{Mg}^{2+}]{\text{ADP-HK}}$ glucose-6-phosphate(G6P) + AMP (Reaction 68)

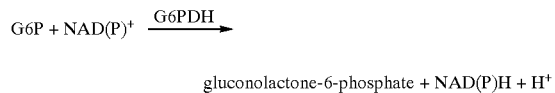

gluconolactone-6-phosphate + NAD(P)H + H⁺

As shown in the above reactions 66, 67 and 68, the present method is the increased reduced NAD (P). The method has no disadvantages as like in the conventional reduced method. Furthermore, it needs not to remove lactate dehydrogenase in the specimen. As a result, the present method shows superior result.

The methods for assay of enzyme, which generate ADP in the specimen, or its substrate of the present invention are explained in the following examples but are not limited within these examples.

EMBODIMENTS OF THE INVENTION

Figure 1:
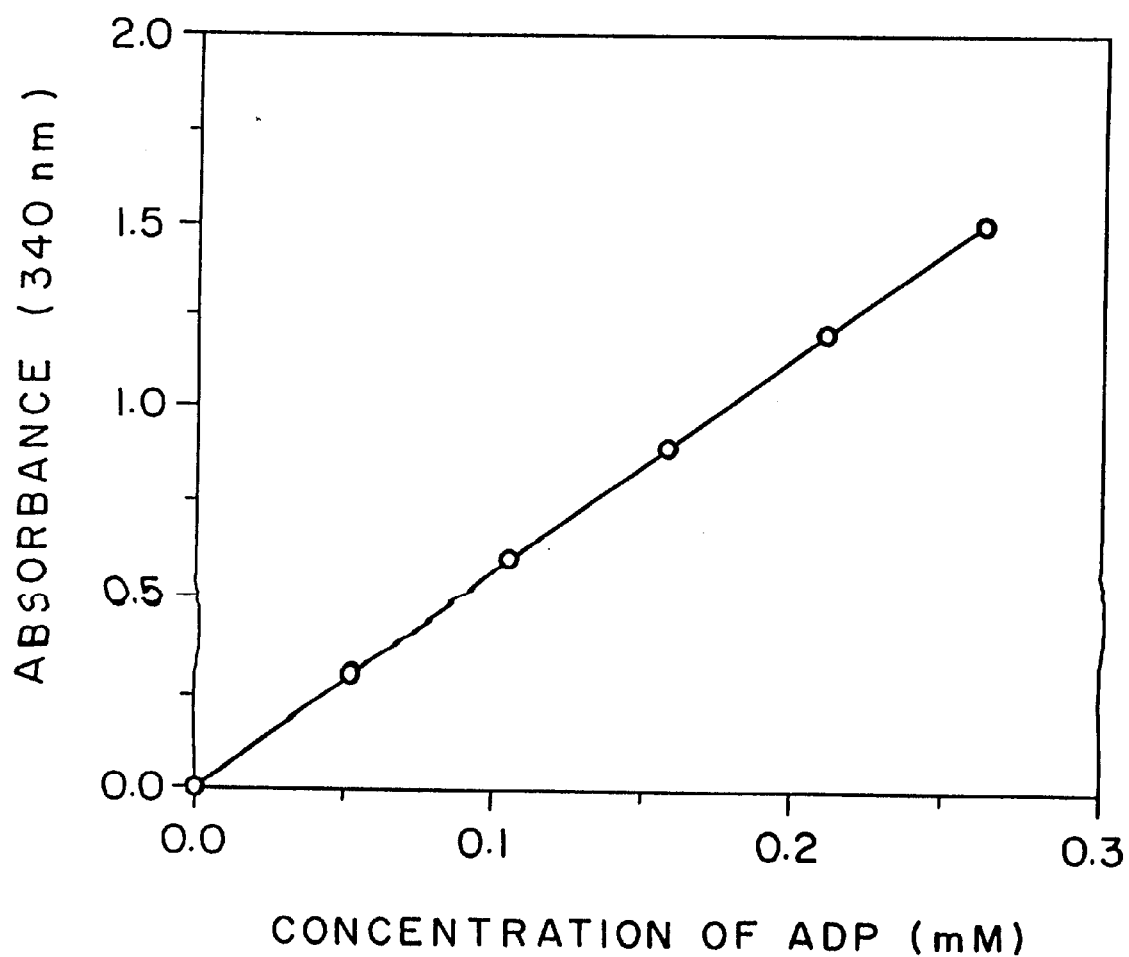
FIG. 1 Standard curve for assaying ADP using magnesium ion at 37° C. in this invention.

The present invention is explained in details by examples and referential examples, but the present invention are not limited within these examples and referential examples.

Referential Example

Assay method of enzyme activity of ADP-HK

| Reagents for assay | |
|---|---|
| 50 mM | Tris-HCl buffer solution (pH 7.5) |
| 20 mM | glucose |
| 2 mM | ADP |
| 2 mM | MgCl$_2$ |
| 5 U/ml | G6PDH |
| 0.025% | NBT (nitrotetrazolium blue) |
| 1 mM | NADP |
| 1% | Triton X-100 |
| 5 U/ml | diaphorase (NADPH) |

After preheating the reagent for assay at 37° C. for 1 minute, enzyme solution 0.02 ml was added and the reaction mixture was reacted for 10 minutes. The reaction was terminated by adding 0.1N HCl 2 ml, and the optical density of the reaction mixture was measured at 550 nm using optical path 1.0 within 5 minutes (As). Optical absorption of the blank was measuring using distilled water 0.02 ml in place of the enzyme solution (Ab). Difference in the absorption in use of enzyme solution (As) and the blank thereof (Ab), i.e. (As−Ab), is used to measure enzyme activity. A unit of enzyme is defined as an amount of enzyme which generates 1 $\mu$ mole of reduced NADP in 1 minute at 37° C. as shown in the following equaltion.

Enzyme unit (U/ml)=(As−Ab)×0.795×dilution rate of enzyme

[Preparation of ADP-HK]
Culture of Pyrococcus furiosus DSM3638

| Culture composition | |
|---|---|
| 0.1% | Yeast extract |
| 0.5% | triptone |
| 0.72% | maltose |
| 2.39% | NaCl |
| 0.4% | Na$_2$SO$_4$ |
| 0.07% | KCl |
| 0.02% | NaHCO$_3$ |
| 0.01% | KBr |
| 0.03% | H$_3$BO$_4$ |
| 1.08% | MgCl$_2$ |
| 0.15% | CaCl$_2$ |
| 0.0025% | SrCl$_2$ |
| 0.025% | NH$_4$Cl |
| 0.014% | K$_2$HPO$_4$ |
| 0.1% | CH$_3$COONa |
| 0.0015% | N (COOH)$_3$ |
| 0.0005% | MnSO$_4$ |
| 0.0014% | FeSO$_4$ |
| 0.0002% | NiCl$_2$ |
| 0.0001% | CoSO$_4$ |
| 0.0001% | ZnSO$_4$ |
| 0.00001% | CuSO$_4$ |
| 0.000001% | Na$_2$WO$_4$ |
| 0.000001% | Na$_2$MoO$_4$ |
| 0.1% | cysteine hydrochloride |

Liquid medium (pH 7) 500 ml containing the above culture composition was poured into ten 500 ml Erlenmeyer flasks and sterilized at 120° C. for 20 minutes. A suspension of Pyrococcus furiosus DSM3638, 10 ml, was inoculated thereto, and the medium was cultured with stirring at 95° C. for 20 hours to prepare seed culture. The liquid medium 200 lit./300 lit. tank containing the above culture composition was sterilized, and the seed culture was inoculated thereto, then the inoculated medium was cultured with agitating at 95° C. for 15 hours to obtain 5 mU/mi cultured liquid 200 lit.

[Purification of ADP-HK]

The obtained cultured liquid 200 lit. was centrifuged. The obtained microbial cells was washed with 20 mM Tris-HCl buffer (pH 7.5) containing 0.9% NaCl. The washed cells was suspended in 20 mM Tris-HCl buffer (pH 7.5) to adjust a volume 2 lit. The suspension was sonicated by using sonicator (KUBOTA Inc., INSONATOR 201M) at 180 W for 30 minutes to obtain sonicated cell suspension.

The sonicated suspension was centrifuged at 8000 rpm for 30 minutes to obtain supernatant solution 1.8 lit. (enzyme activity 980 U). The supernatant was dialyzed by using dialysis tube against Tris-HCl buffer (pH 7.5) 8 lit. at 5° C. for overnight. The dialyzate was applied in the column of DEAE-Sepharose FF (Pharmacia Inc.) 200 ml (2.6×38 cm) buffered with 10 mM Tris-HCl buffer (pH 7.5), and was eluted by linear gradient elution of 0–1 mole NaCl. Active fraction (950 U) was eluted at the concentration of 0.08–0.1 mole of NaCl. NaCl was dissolved to 4 M in the obtained active fraction, and the solution was applied in the column of Phenyl-Sepharose FF (Pharmacia Inc.) 200 ml (2.6×38 cm) buffered with 4M NaCl, and was eluted by linear gradient elution of 4–0 mole NaCl.

The active fraction (900 U) was obtained in 0.02–0.07 mole NaCl concentraion. The thus obtained active fraction was dialyzed against 10 mM Tris-HCl buffer (pH 7.5) 8 lit. at 5° C. for overnight. The dialyzate was applied in the column of hydroxyapatite (Pentax Inc.) 100 ml (2.6×19 cm) buffered with 10 mM Tris-HCl buffer (pH 7.5), and was eluted by linear gradient elution of 0–0.5 mole phosphate buffer (pH 7.5). Active fraction (850 U) was eluted at the concentration of 0.02–0.03 mole of phosphate buffer. The thus obtained enzyme solution was lyophilized to obtain enzyme powder 5 mg (170 U/mg).
Biochemical Properties of ADP-HK was as Follows.
[Biochemical properties of ADP-HK]
(1) Enzyme action
Enzyme action using glucose as a substrate is shown as follows.

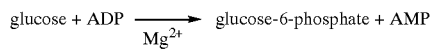

$$\text{glucose} + \text{ADP} \xrightarrow{Mg^{2+}} \text{glucose-6-phosphate} + \text{AMP}$$

(2) Molecular weight
Molecular weight of ADP-HK measured by gel-filtration using TSK-G3000SWxL(0.75 ×30 cm)(Toso Corp.) was 100000±5000.
(3) Optimum pH : pH 6.0–7.0 (phosphate buffer).
(4) Optimum temperature : 80–100° C. Consequently, the microorganism was defined as super thermophile ADP-HK.

EXAMPLE 1

Quantitative Assay of ADP Using Magnesium Ion at 37° C.

| Reagents | |
|---|---|
| 50 mM | Tris-HCl buffer solution (pH 7.5) |
| 20 mM | glucose |
| 5 U/ml | G6PDH |
| 1 mM | NADP |
| 2 mM | MgCl$_2$ |
| 5 U/ml | ADP-HK |

Assay Method

ADP aqueous solution was prepared at concentration of 2.6 mM, 5.2 mM, 7.8 mM, 10.4 mM and 13 mM to prepare ADP sample. ADP sample 20μl was added to the reagents for assay 1 ml, and the optical absorption at 340 nm was measured after incubation at 37° C. for 5 minutes with a control of the blank solution. As shown in FIG. 1 (horizontal axis: shown as final concentration), ADP could be assayed quantitatively.

EXAMPLE 2

Quantitative Assay of ADP Using Cobalt Ion at 37° C.

| Reagents | |
|---|---|
| 50 mM | Tris-HCl buffer solution (pH 7.5) |
| 20 mM | glucose |
| 5 U/ml | G6PDH |
| 1 mM | NADP |
| 2 mM | CoCl$_2$ |
| 10 U/ml | ADP-HK |

Assay Method

Figure 2:
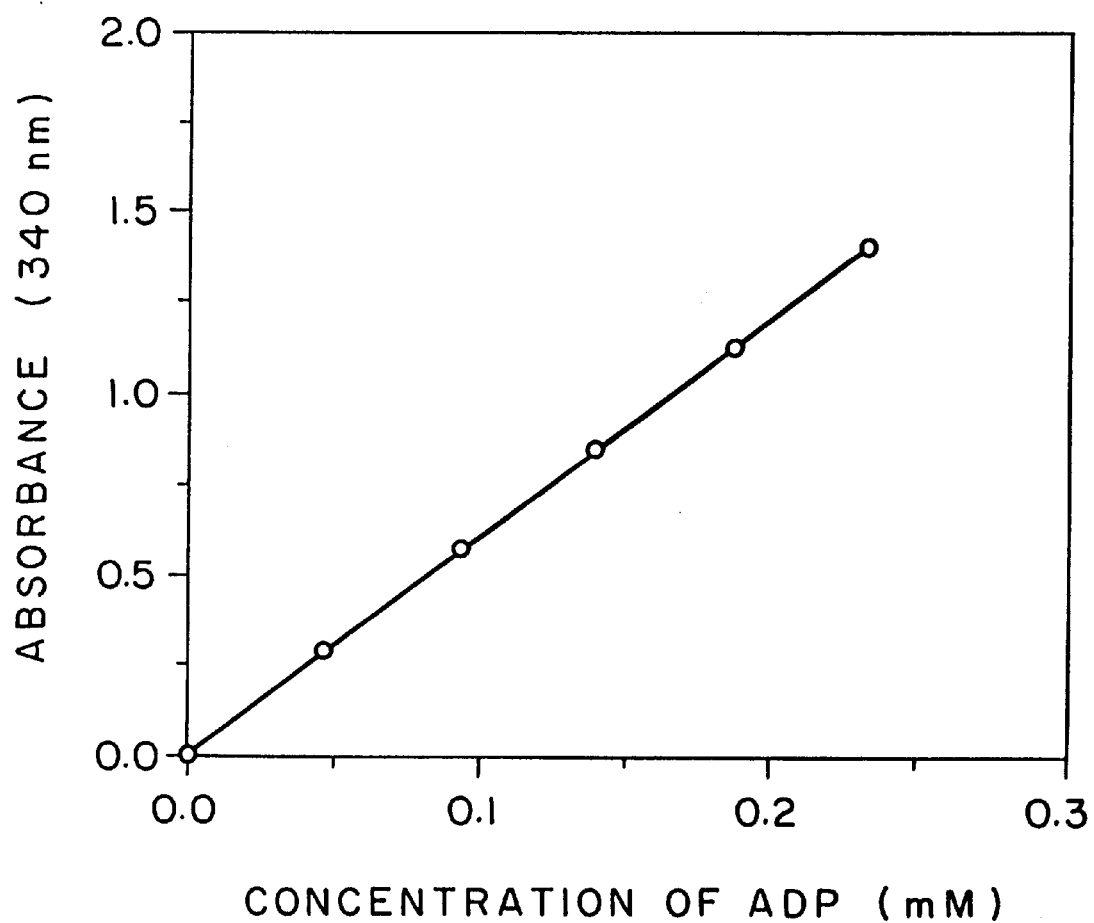
FIG. 2 Standard curve for assaying ADP using cobalt ion at 37° C. in this invention.

ADP aqueous solution was prepared at concentration of 2.3 mM, 4.6 mM, 6.9 mM, 9.2 mM and 11.5 mM to prepare ADP sample. ADP sample 20 μl was added to the reagents for assay 1 ml, and the optical absorption at 340 nm was measured after incubation at 37° C. for 5 minutes with a control of the blank solution. As shown in FIG. 2, ADP could be assayed quantitatively.

EXAMPLE 3

Quantitative Assay of ADP Using Manganese Ion at 37° C.

| Reagents | |
|---|---|
| 50 mM | Tris-HCl buffer solution (pH 7.5) |
| 20 mM | glucose |
| 5 U/ml | G6PDH |
| 1 mM | NADP |
| 2 mM | MnCl$_2$ |
| 10 U/ml | ADP-HK |

Assay Method

Figure 3:
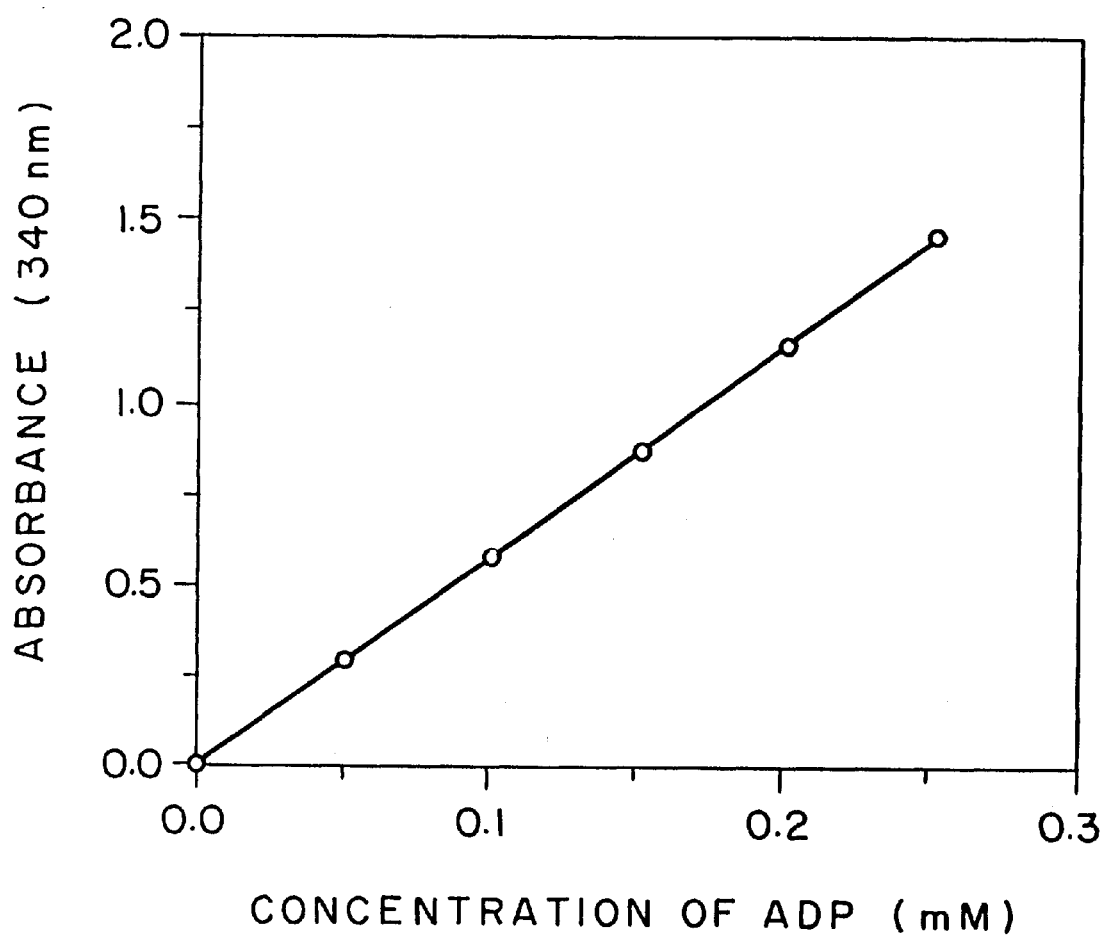
FIG. 3 Standard curve for assaying ADP using manganese ion at 37° C. in this invention.

ADP aqueous solution was prepared at concentration of 2.5 mM, 5.0 mM, 7.5 mM, 10.0 mM and 12.5 mM to prepare ADP sample. ADP sample 20 μl was added to the reagents for assay 1 ml, and the optical absorption at 340 nm was measured after incubation at 37° C. for 5 minutes with a control of the blank solution. As shown in FIG. 3, ADP could be assayed quantitatively.

EXAMPLE 4

Quantitative Assay of ADP Using Magnesium Ion at 20° C.

| Reagents | |
|---|---|
| 50 mM | Tris-HCl buffer solution (pH 7.5) |
| 20 mM | glucose |
| 5 U/ml | G6PDH |
| 1 mM | NADP |
| 2 mM | MgCl$_2$ |
| 10 U/ml | ADP-HK |

Assay Method

Figure 4:
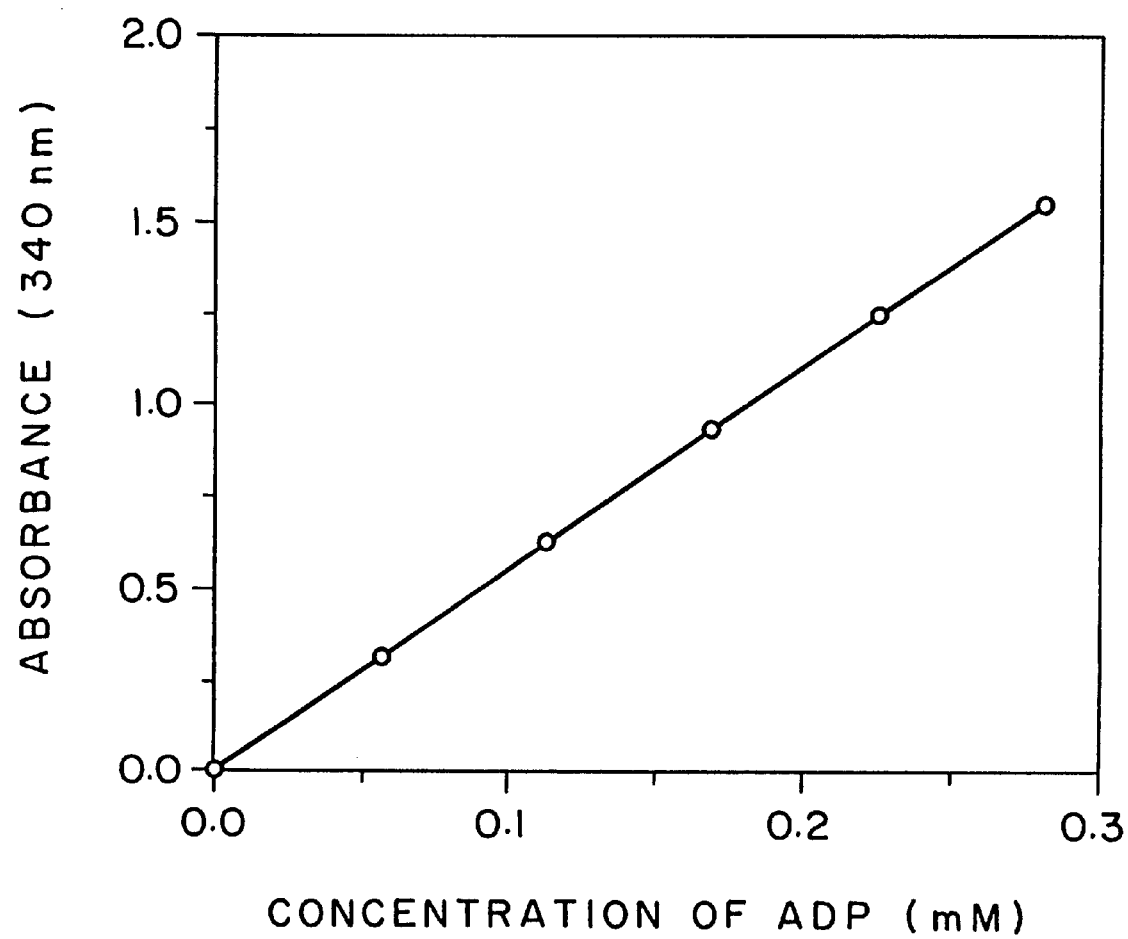
FIG. 4 Standard curve for assaying ADP using magnesium ion at 20° C. in this invention.

ADP aqueous solution was prepared at concentration of 2.8 mM, 5.6 mM, 8.4 mM, 11.2 mM and 14 mM to prepare ADP sample. ADP sample 20μl was added to the reagents for assay 1 ml, and the optical absorption at 340 nm was measured after incubation at 20° C. for 5 minutes with a control of the blank solution. As shown in FIG. 4, ADP could be assayed quantitatively.

EXAMPLE 5

Quantitative Assay of ADP Using Magnesium Ion at 40° C.

| Reagents | |
|---|---|
| 50 mM | Tris-HCl buffer solution (pH 7.5) |
| 20 mM | glucose |
| 5 U/ml | G6PDH |
| 1 mM | NADP |
| 2 mM | MgCl$_2$ |
| 10 U/ml | ADP-HK |

Assay Method

Figure 5:
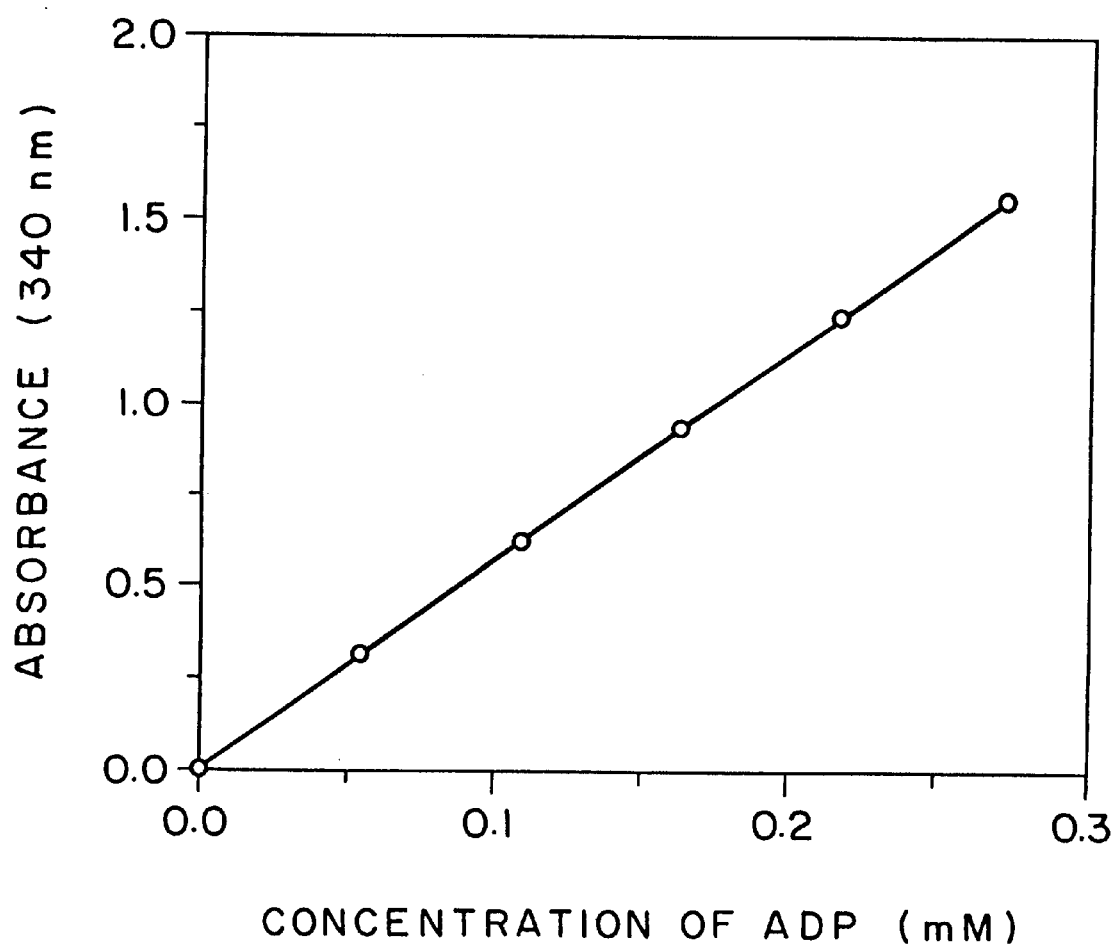
FIG. 5 Standard curve for assaying ADP using magnesium ion at 40° C. in this invention.

ADP aqueous solution was prepared at concentration of 2.7 mM, 5.4 mM, 8.1 mM, 10.8 mM and 13.5 mM to prepare ADP sample. ADP sample 20 μl was added to the reagents for assay 1 ml, and the optical absorption at 340 nm was measured after incubation at 40° C. for 5 minutes with a control of the blank solution. As shown in FIG. 5, ADP could be assayed quantitatively.

EXAMPLE 6

Quantitative Assay of Urea Using Magnesium Ion at 37° C.

| Reagents | |
|---|---|
| 50 mM | Tris-HCl buffer solution (pH 7.5) |
| 30 U/ml | urea amidelyase |
| 2 mM | ATP |
| 10 mM | KCl |
| 8 mM | KHCO$_3$ |
| 20 mM | glucose |
| 5 U/ml | G6PDH |
| 1 mM | NADP |
| 2 mM | MgCl$_2$ |
| 5 U/ml | ADP-HK |

Assay Method

Figure 6:
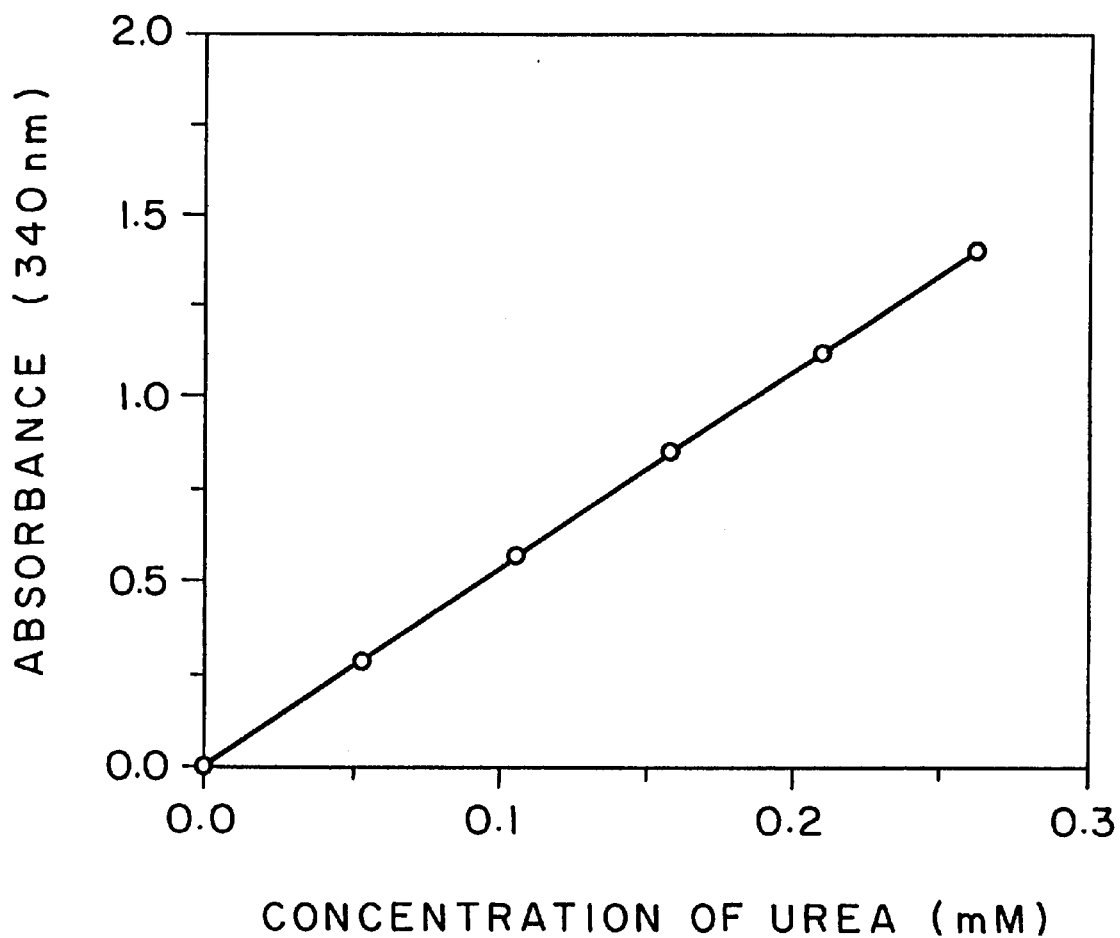
FIG. 6 Standard curve for assaying urea uaing magnesium ion at 37° C. in this invention.

Urea aqueous solution was prepared at concentration of 2.6 mM, 5.2 mM, 7.8 mM, 10.4 mM and 13 mM to prepare urea sample. Urea sample 20 μl was added to the reagents for assay 1 ml, and the optical absorption at 340 nm was measured after incubation at 37° C. for 5 minutes with a control of the blank solution. As shown in FIG. 6, urea could be assayed quantitatively.

EXAMPLE 7

Quantitative Assay of Creatinine Using Magnesium Ion at 37° C. (1)

| Reagents | |
|---|---|
| 50 mM | Tris-HCl buffer solution (pH 7.5) |
| 100 U/ml | creatinine amide hydrolase |
| 5 U/ml | creatine kinase |
| 2 mM | ATP |
| 20 mM | glucose |
| 5 U/ml | G6PDH |
| 1 mM | NADP |
| 2 mM | MgCl$_2$ |
| 5 U/ml | ADP-HK |

Assay Method

Figure 7:
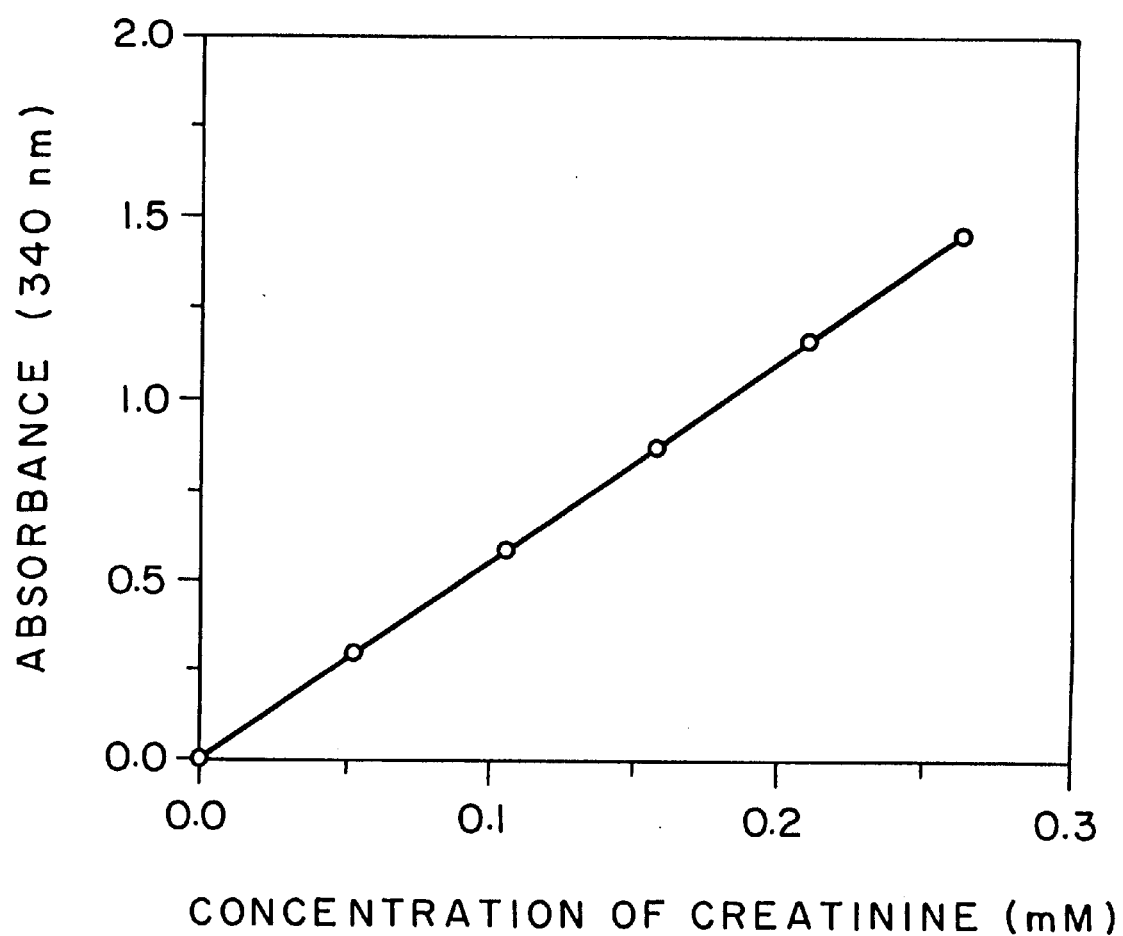
FIG. 7 Standard curve for assaying creatinine using magnesium ion at 37° C. in this invention.

Creatinine aqueous solution was prepared at concentration of 2.6 mM, 5.2 mM, 7.8 mM, 10.4 mM and 13 mM to prepare creatinine sample. Creatinine sample 20 μl was added to the reagents for assay 1 ml, and the optical absorption at 340 nm was measured after incubation at 37° C. for 5 minutes with a control of the blank solution. As shown in FIG. 7, creatinine could be assayed quantitatively.

EXAMPLE 8

Quantitative Assay of Creatinine Using Magnesium Ion at 37° C. (2)

| Reagents | |
|---|---|
| 50 mM | Tris-HCl buffer solution (pH 7.5) |
| 10 U/ml | creatinine deiminase |
| 10 U/ml | N-methyl hydantoinase |
| 2 mM | ATP |
| 20 mM | glucose |
| 5 U/ml | G6PDH |
| 1 mM | NADP |
| 2 mM | MgCl$_2$ |
| 5 U/ml | ADP-HK |

Assay Method

Figure 8:
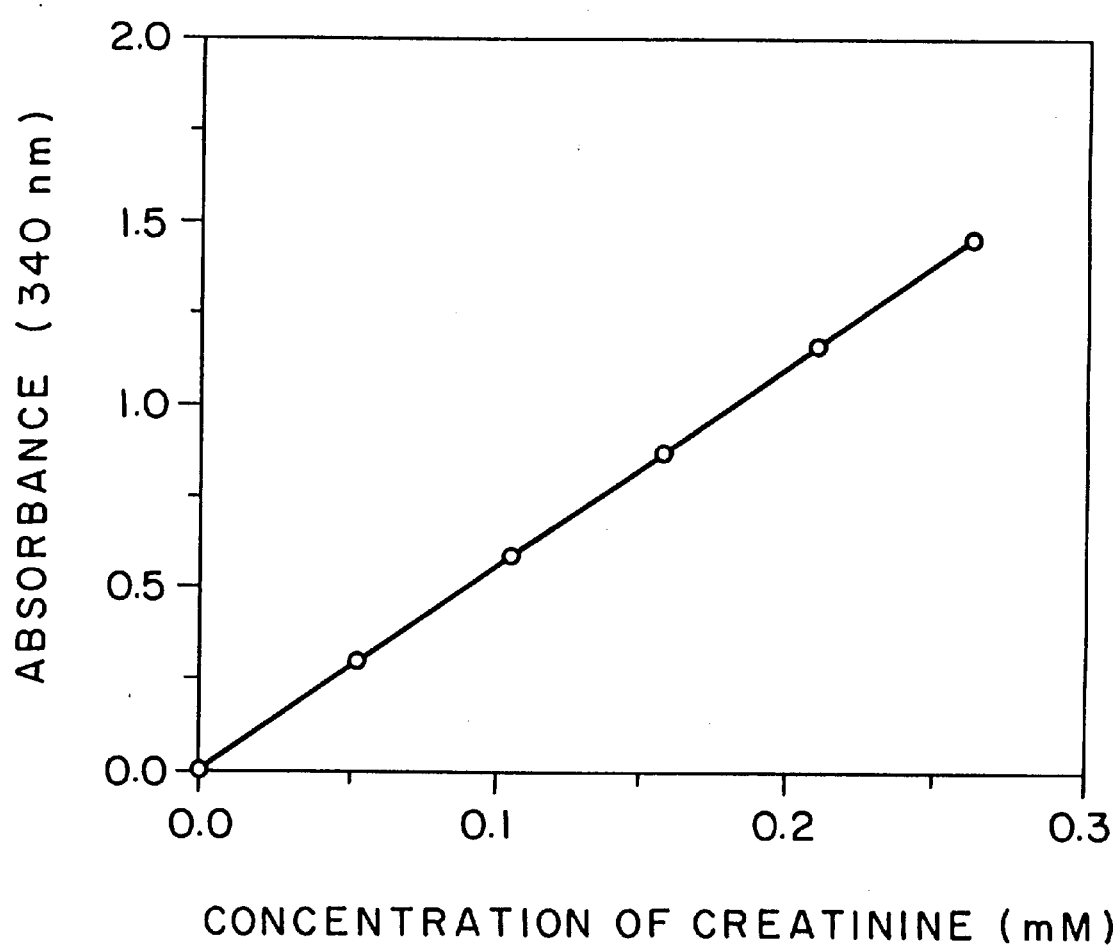
FIG. 8 Standard curve for assaying creatinine using magnesium ion at 37° C. in this invention.

Creatinine aqueous solution was prepared at concentration of 2.7 mM, 4.3 mM, 7.9 mM, 10.5 mM and 13 mM to prepare creatinine sample. Creatinine sample 20 μl was added to the reagents for assay 1 ml, and the optical absorption at 340 nm was measured after incubation at 37° C. for 5 minutes with a control of the blank solution. As shown in FIG. 8, creatinine could be assayed quantitatively.

EXAMPLE 9

Quantitative Assay of Creatine Using Magnesium Ion at 37° C.

| Reagents | |
|---|---|
| 50 mM | Tris-HCl buffer solution (pH 7.5) |
| 5 U/ml | creatine kinase |
| 2 mM | ATP |
| 20 mM | glucose |
| 5 U/ml | G6PDH |
| 1 mM | NADP |
| 2 mM | MgCl$_2$ |
| 5 U/ml | ADP-HK |

Assay Method

Figure 9:
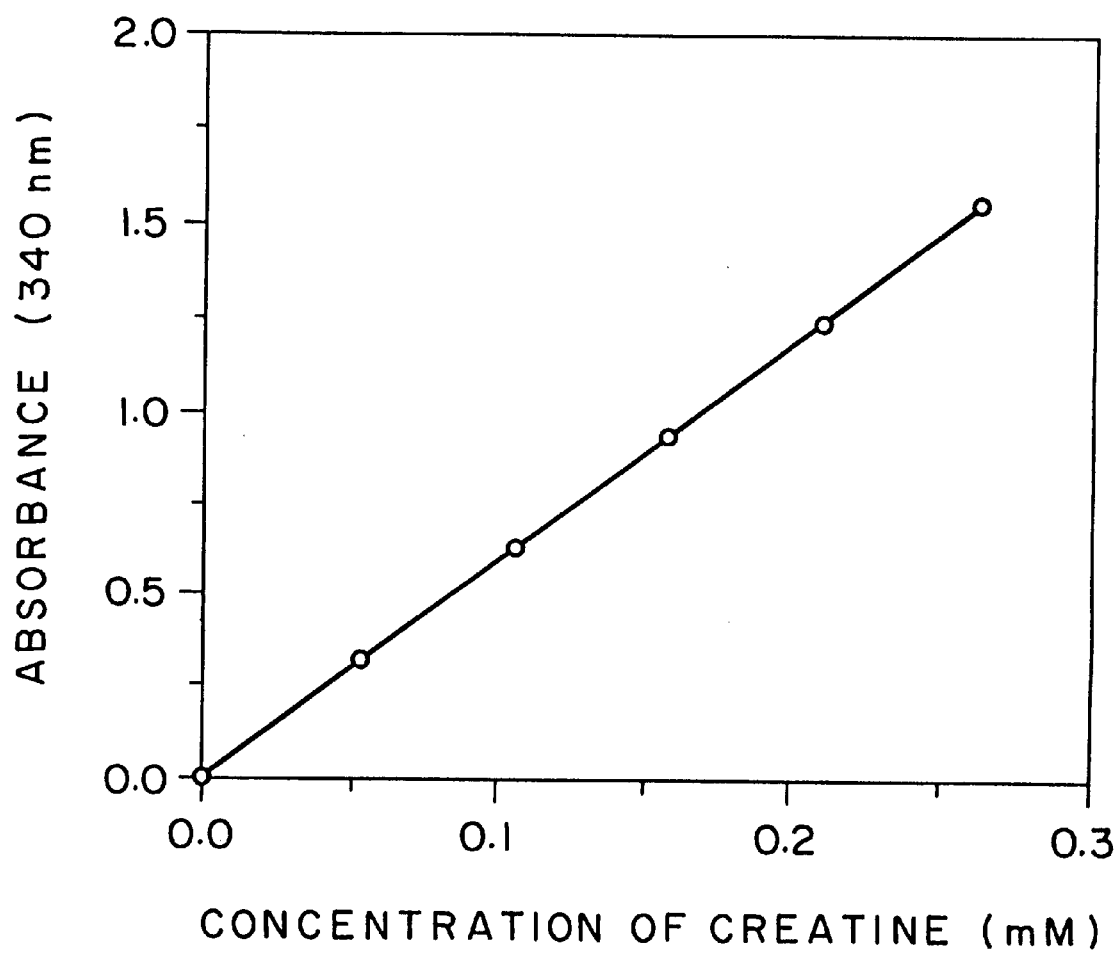
FIG. 9 Standard curve for assaying creatine uaing magnesium ion at 37° C. in this invention.

Creatine aqueous solution was prepared at concentration of 2.6 mM, 5.2 mM, 7.8 mM, 10.4 mM and 13 mM to prepare creatine sample. Creatine sample 20 μl was added to the reagents for assay 1 ml, and the optical absorption at 340 nm was measured after incubation at 37° C. for 5 minutes with a control of the blank solution. As shown in FIG. 9, creatine could be assayed quantitatively.

EXAMPLE 10

Quantitative Assay of Glycerol Using Magnesium Ion at 37° C.

| Reagents | |
|---|---|
| 50 mM | Tris-HCl buffer solution (pH 7.5) |
| 5 U/ml | glycerol kinase |
| 2 mM | ATP |
| 20 mM | glucose |
| 5 U/ml | G6PDH |
| 1 mM | NADP |
| 2 mM | MgCl$_2$ |
| 5 U/ml | ADP-HK |

Assay Method

Figure 10:
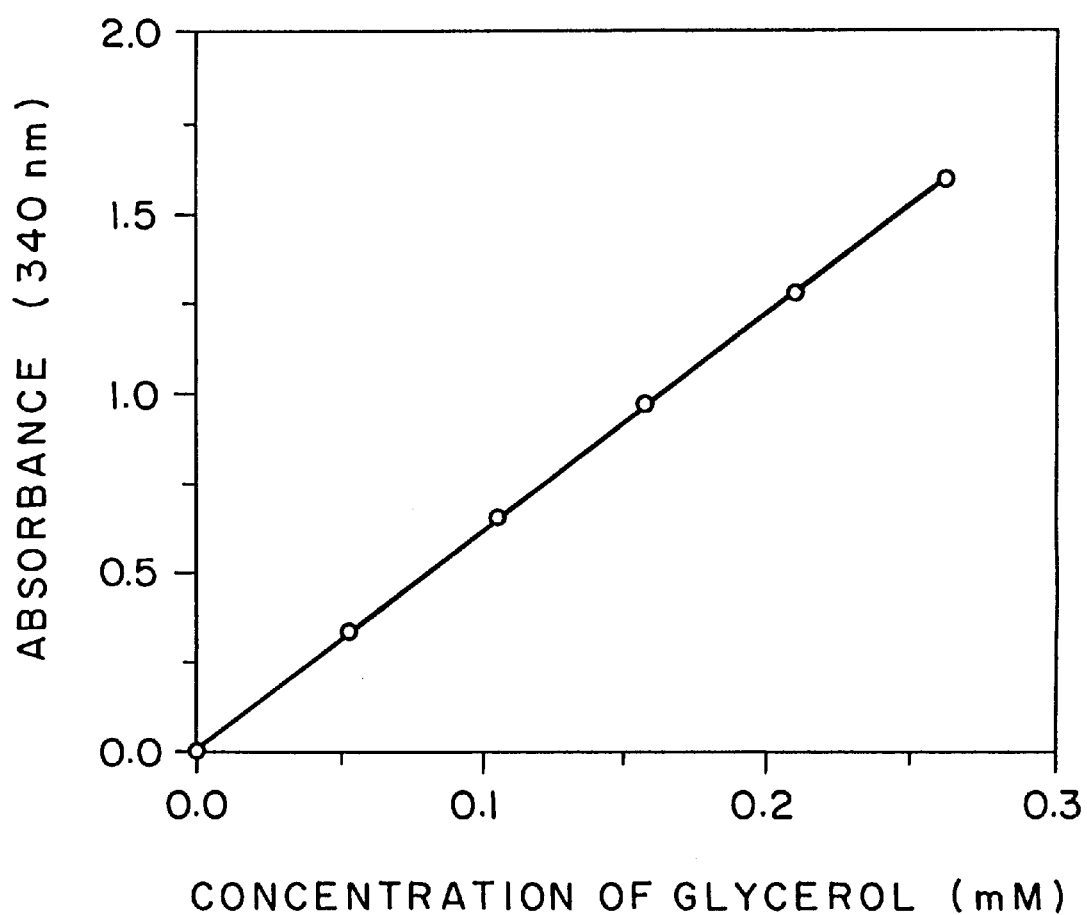
FIG. 10 Standard curve for assaying glycerol using magnesium ion at 37° C. in this invention.

Glycerol aqueous solution was prepared at concentration of 2.6 mM, 5.2 mM, 7.8 mM, 10.4 mM and 13 mM to prepare glycerol sample. Glycerol sample 20 μl was added to the reagents for assay 1 ml, and the optical absorption at 340 nm was measured after incubation at 37° C. for 5 minutes with a control of the blank solution. As shown in FIG. 10, glycerol could be assayed quantitatively. Liberated glycerol from triglycerol by an action of lipase, or that from phosphatidylglycerol by an action of phospholipase D could be assayed.

EXAMPLE 11

Quantitative Assay of Choline Using Magnesium Ion at 37° C.

| Reagents | | |
|---|---|---|
| 50 | mM | Tris-HCl buffer solution (pH 7.5) |
| 5 | U/ml | choline kinase |
| 2 | mM | ATP |
| 20 | mM | glucose |
| 5 | U/ml | G6PDH |
| 1 | mM | NADP |
| 2 | mM | $MgCl_2$ |
| 5 | U/ml | ADP-HK |

Assay Method

Figure 11:
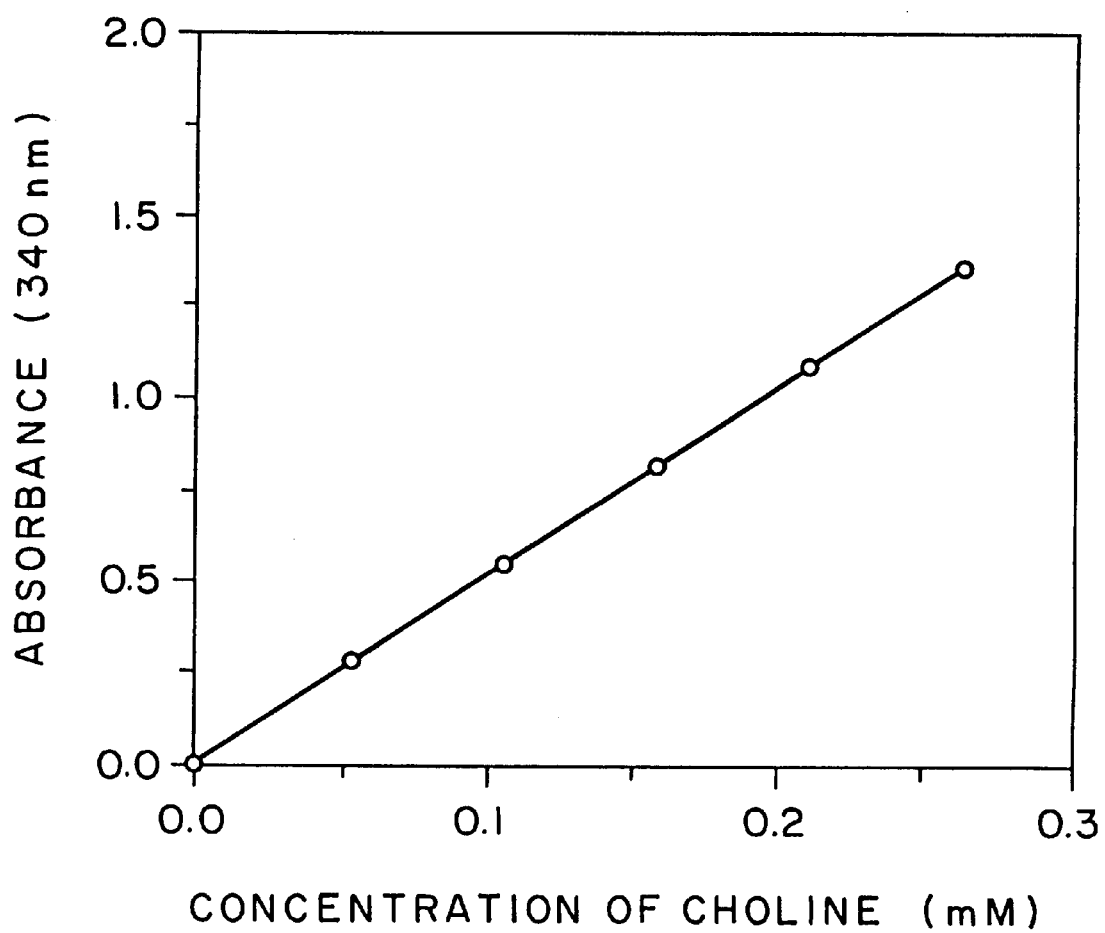
FIG. 11 Standard curve for assaying choline using magnesium ion at 37° C. in this invention.

Choline hydrochloride aqueous solution was prepared at concentration of 2.6 mM, 5.2 mM, 7.8 mM, 10.4 mM and 13 mM to prepare choline hydrochloride sample. Choline hydrochloride sample 20 µl was added to the reagents for assay 1 ml, and the optical absorption at 340 nm was measured after incubation at 37° C. for 5 minutes with a control of the blank solution. As shown in FIG. 11, choline could be assayed quantitatively. Liberated choline from phospholipase by an action of phospholipase D could be assayed.

EXAMPLE 12

Quantitative Assay of Glutamate Using Magnesium Ion at 37° C.

| Reagents | | |
|---|---|---|
| 50 | mM | Tris-HCl buffer solution (pH 7.5) |
| 10 | U/ml | glutamine synthetase |
| 10 | mM | $NH_4Cl$ |
| 2 | mM | ATP |
| 20 | mM | glucose |
| 5 | U/ml | G6PDH |
| 1 | mM | NADP |
| 2 | mM | $MgCl_2$ |
| 5 | U/ml | ADP-HK |

Assay Method

Figure 12:
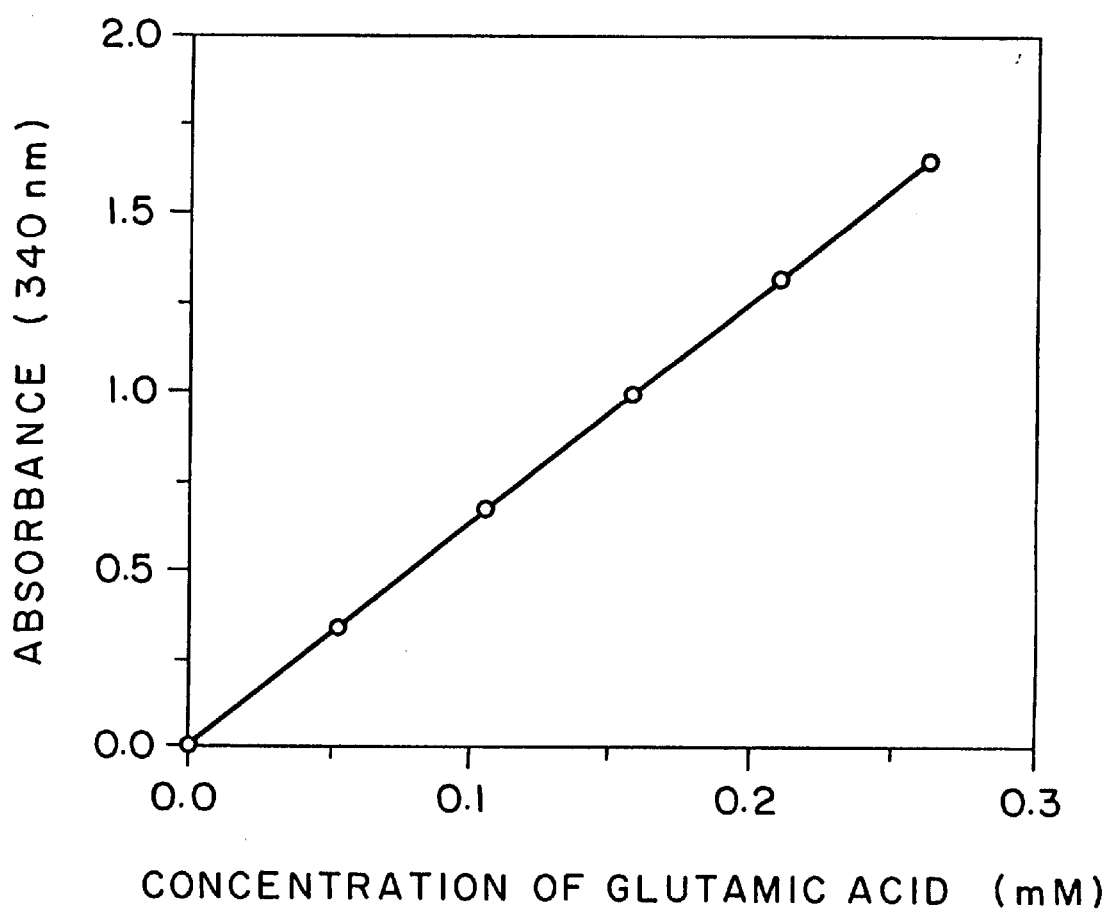
FIG. 12 Standard curve for assaying glutamate using magnesium ion at 37° C. in this invention.

L-glutamate aqueous solution was prepared at concentration of 2.6 mM, 5.2 mM, 7.8 mM, 10.4 mM and 13 mM to prepare L-glutamate sample. L-glutamate sample 20 µl was added to the reagents for assay 1 ml, and the optical absorption at 340 nm was measured after incubation at 37° C. for 5 minutes with a control of the blank solution. As shown in FIG. 12, L-glutamate could be assayed quantitatively. Liberated L-glutamate by an action of aspartate transferase (GOT) or alanine transferase (GPT) could be assayed.

EXAMPLE 13

Quantitative Assay of Urea Using Cobalt Ion at 37° C.

| Reagents | | |
|---|---|---|
| 50 | mM | Tris-HCl buffer solution (pH 7.5) |
| 30 | U/ml | urea amidelyase |
| 2 | mM | ATP |
| 10 | mM | KCl |
| 8 | mM | $KHCO_3$ |
| 20 | mM | glucose |
| 5 | U/ml | G6PDH |
| 1 | mM | NADP |
| 2 | mM | $CoCl_2$ |
| 10 | U/ml | ADP-HK |

Assay Method

Figure 13:
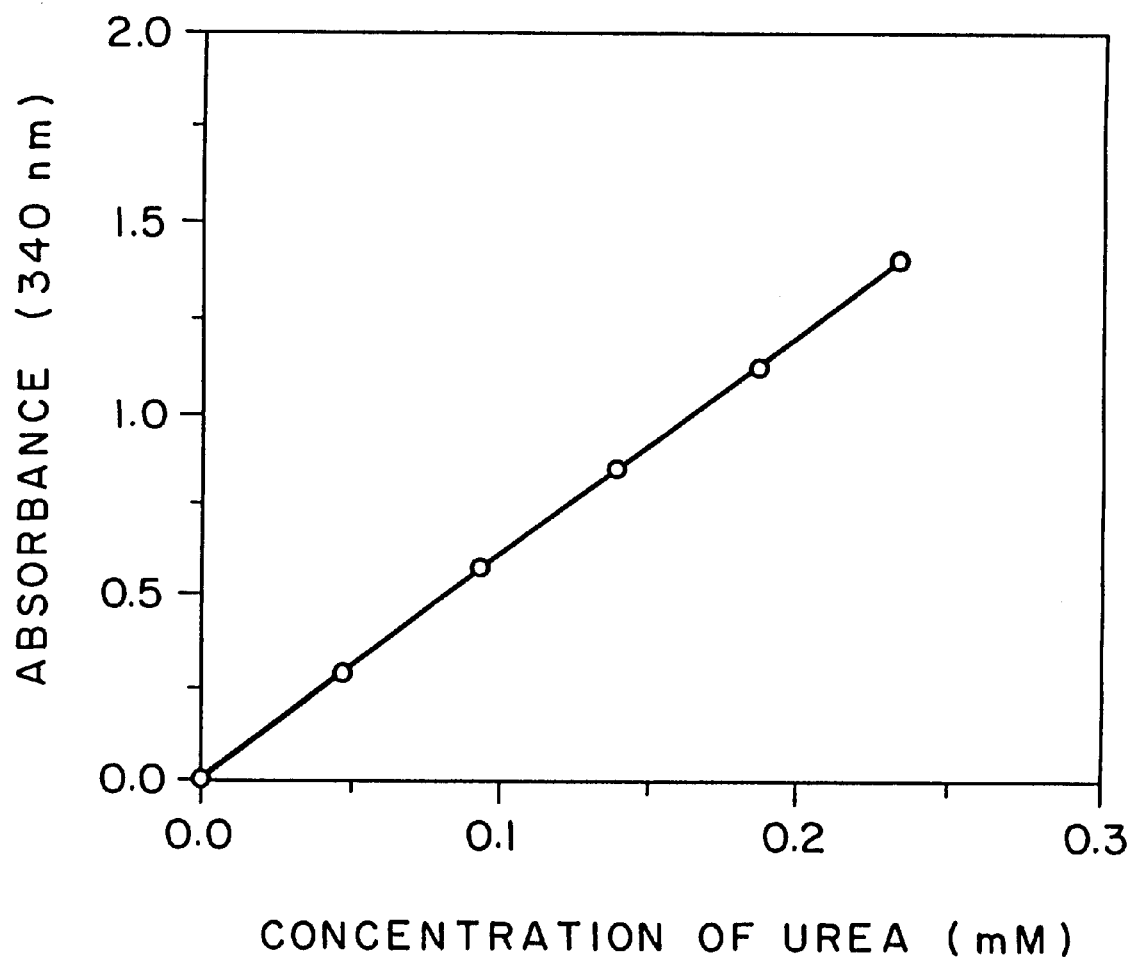
FIG. 13 Standard curve for assaying urea using cobalt ion at 37° C. in this invention.

Urea aqueous solution was prepared at concentration of 2.3 mM, 4.6 mM, 6.9 mM, 9.2 mM and 11.5 mM to prepare urea sample. Urea sample 20 µl was added to the reagents for assay 1 ml, and the optical absorption at 340 nm was measured after incubation at 37° C. for 5 minutes with a control of the blank solution. As shown in FIG. 13, urea could be assayed quantitatively.

EXAMPLE 14

Quantitative Assay of Creatinine Using Manganese Ion at 37° C. (1)

| Reagents | | |
|---|---|---|
| 50 | mM | Tris-HCl buffer solution (pH 7.5) |
| 100 | U/ml | creatinine amide hydrolase |
| 5 | U/ml | creatine kinase |
| 2 | mM | ATP |
| 20 | mM | glucose |
| 5 | U/ml | G6PDH |
| 1 | mM | NADP |
| 2 | mM | $MnCl_2$ |
| 10 | U/ml | ADP-HK |

Assay Method

Figure 14:
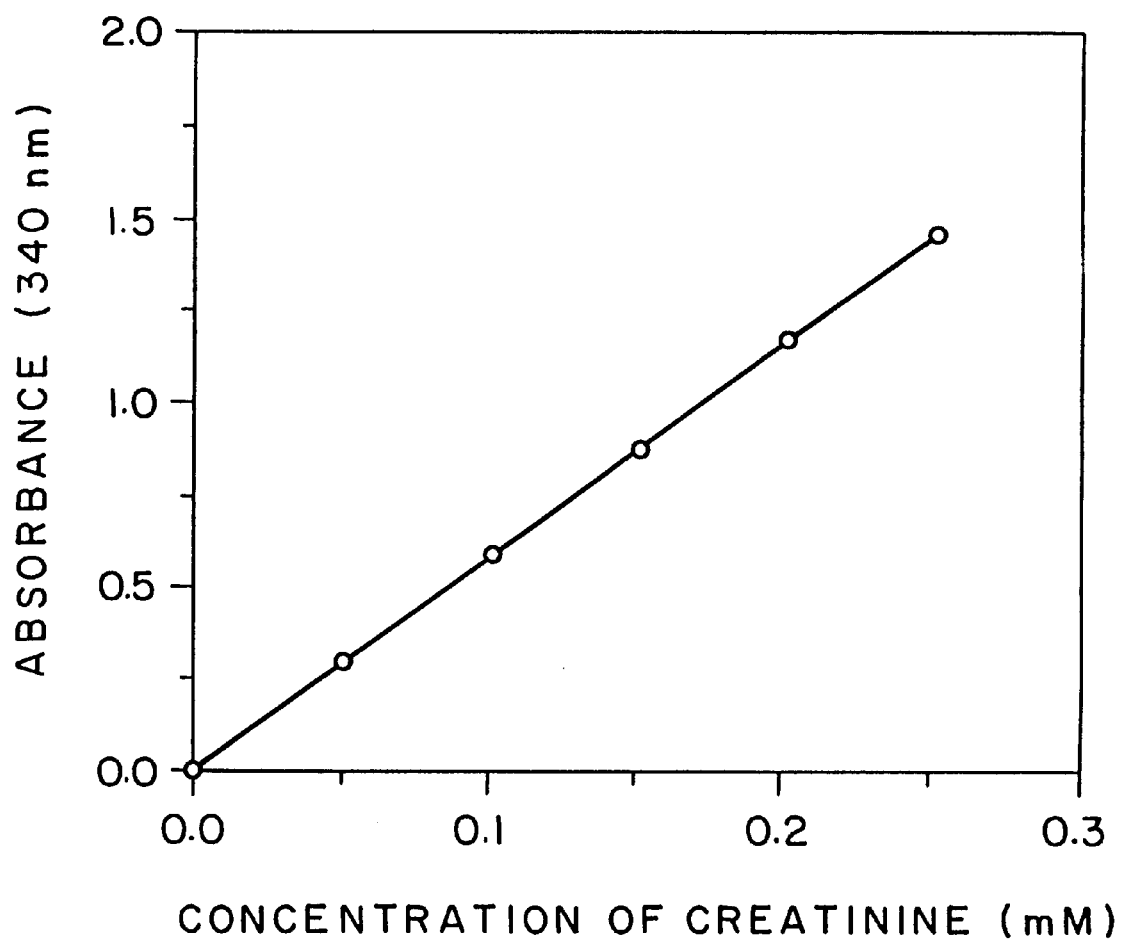
FIG. 14 Standard curve for assaying creatinine using manganese ion at 37° C. in this invention.

Creatinine aqueous solution was prepared at concentration of 2.5 mM, 5.0 mM, 7.5 mM, 10.0 mM and 12.5 mM to prepare creatinine sample. Creatinine sample 20 µl was added to the reagents for assay 1 ml, and the optical absorption at 340 nm was measured after incubation at 37° C. for 5 minutes with a control of the blank solution. As shown in FIG. 14, creatinine could be assayed quantitatively.

EXAMPLE 15

Quantitatively Assay of Creatine Using Magnesium Ion at 20° C.

| Reagents | | |
|---|---|---|
| 50 | mM | Tris-HCl buffer solution (pH 7.5) |
| 5 | U/ml | creatine kinase |
| 5 | U/ml | creatine kinase |
| 2 | M | ATP |
| 20 | mM | glucose |
| 5 | U/ml | G6PDH |
| 1 | mM | NADP |
| 2 | mM | $MgCl_2$ |
| 20 | U/ml | ADP-HK |

Assay Method

Figure 15:
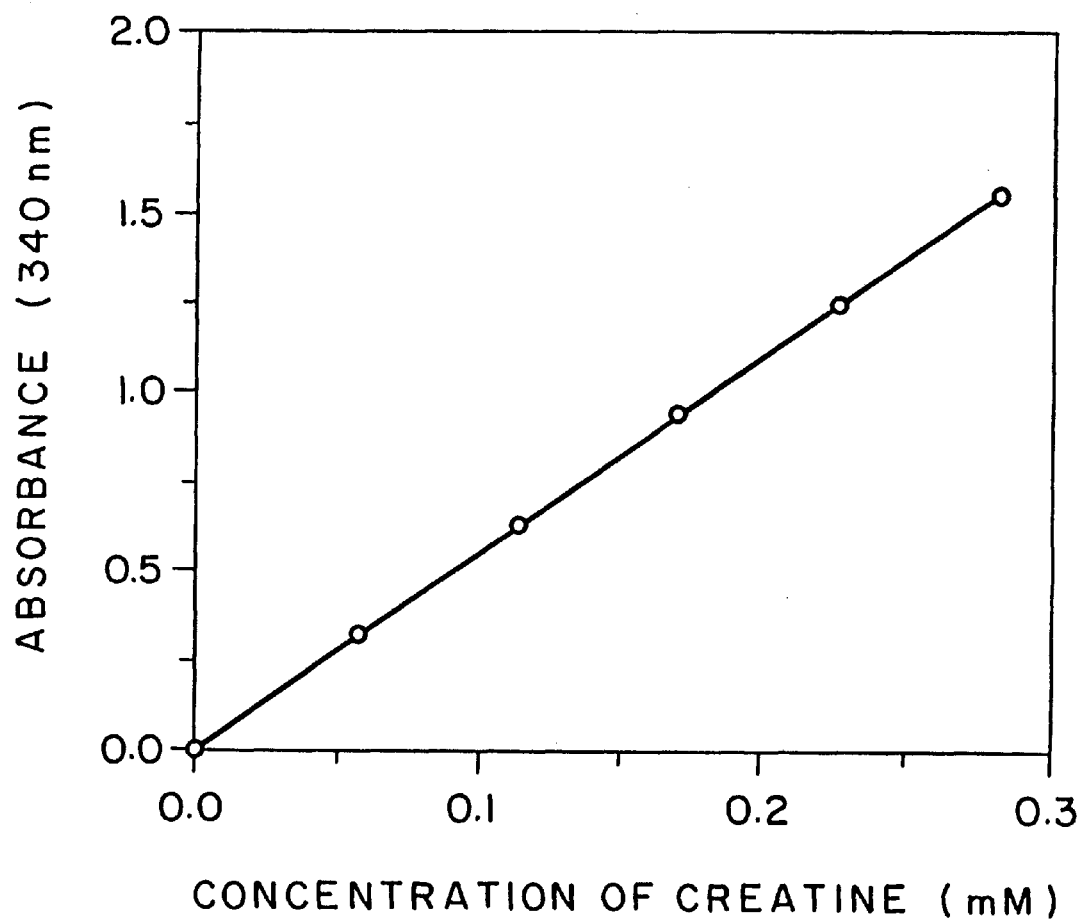
FIG. 15 Standard curve for assaying creatine using magnesium ion at 20° C. in this invention.

Creatine aqueous solution was prepared at concentration of 2.8 mM, 5.6 mM, 8.4 mM, 11.2 mM and 14 mM to prepare creatine sample. Creatine sample 20 µl was added to the reagents for assay 1 ml, and the optical absorption at 340 was measured after incubation at 20° C. for 5 minutes with a control. of the blank solution. As shown in FIG. 15, creatine could be assayed quantitatively.

EXAMPLE 16

Quantitative Assay of Glycerol Using Magnesium Ion at 40° C.

| | | Reagents |
|---|---|---|
| 50 | mM | Tris-HCl buffer solution (pH 7.5) |
| 5 | U/ml | glycerol kinase |
| 2 | mM | ATP |
| 20 | mM | glucose |
| 5 | U/ml | G6PDH |
| 1 | mM | NADP |
| 2 | mM | $MgCl_2$ |
| 5 | U/ml | ADP-HK |

Assay Method

Figure 16:
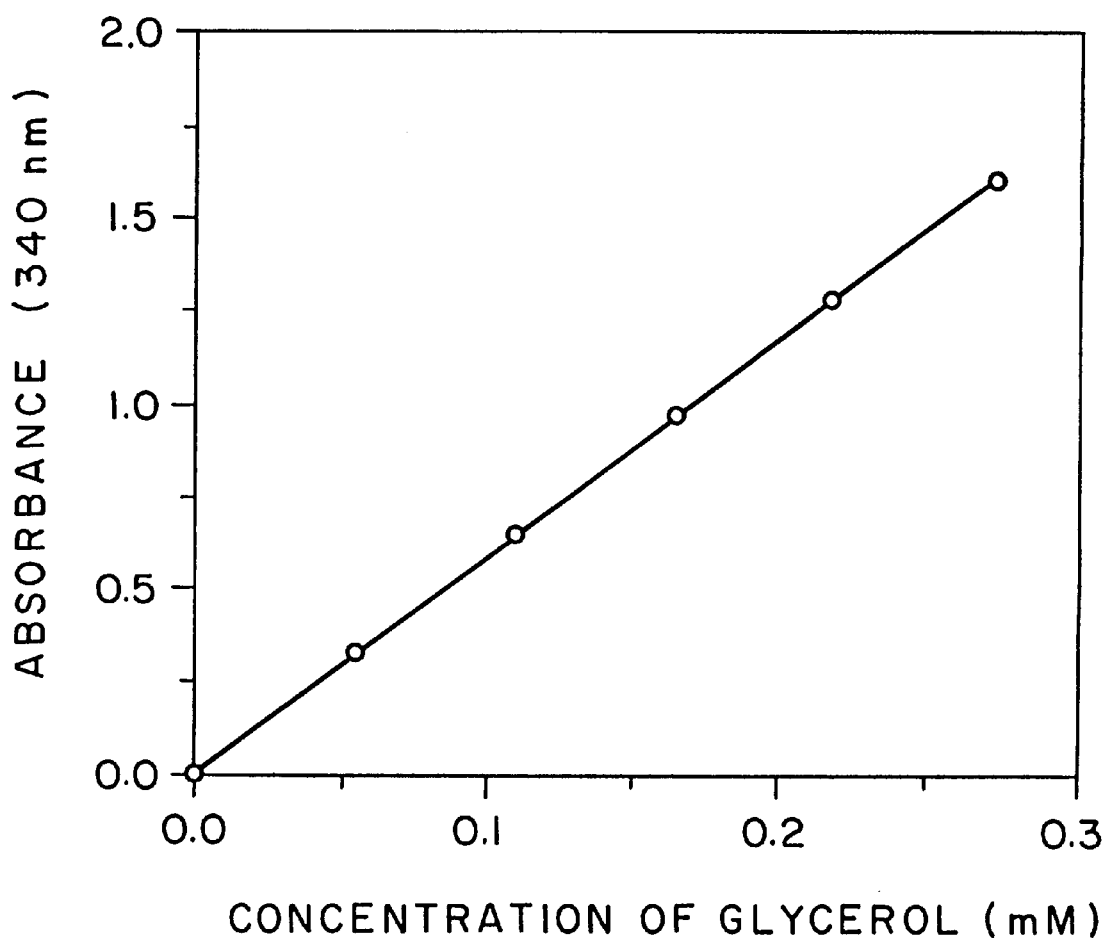
FIG. 16 Standard curve for assaying glycerol using magnesium ion at 40° C. in this invention.

Glycerol aqueous solution was prepared at concentration of 2.7 mM, 5.4 mM, 8.1 mM, 10.8 and 13.5 mM to prepare glycerol sample. Glycerol sample 20 μl was added to the reagents for assay 1 ml, and the optical absorption at 340 nm was measured after incubation at 40° C. for 5 minutes with a control of the blank solution. As shown in FIG. 16, glycerol could be assayed quantitatively. Liberated glycerol from triglycerol by an action of lipase, or that from phosphatidylglycerol by an action of phospholipase D could be assayed.

Referential Example 2

Qualitatively of ADO at 50° C.

| | | Reagents |
|---|---|---|
| 50 | mM | Tris-HCl buffer solution (pH 7.5) |
| 20 | mM | glucose |
| 0.5 | U/ml | G6PDH |
| 1 | mM | NADP |
| 2 | mM | $MgCl_2$ |
| 5 | U/ml | ADP-HK |

Assay Method

Figure 17:
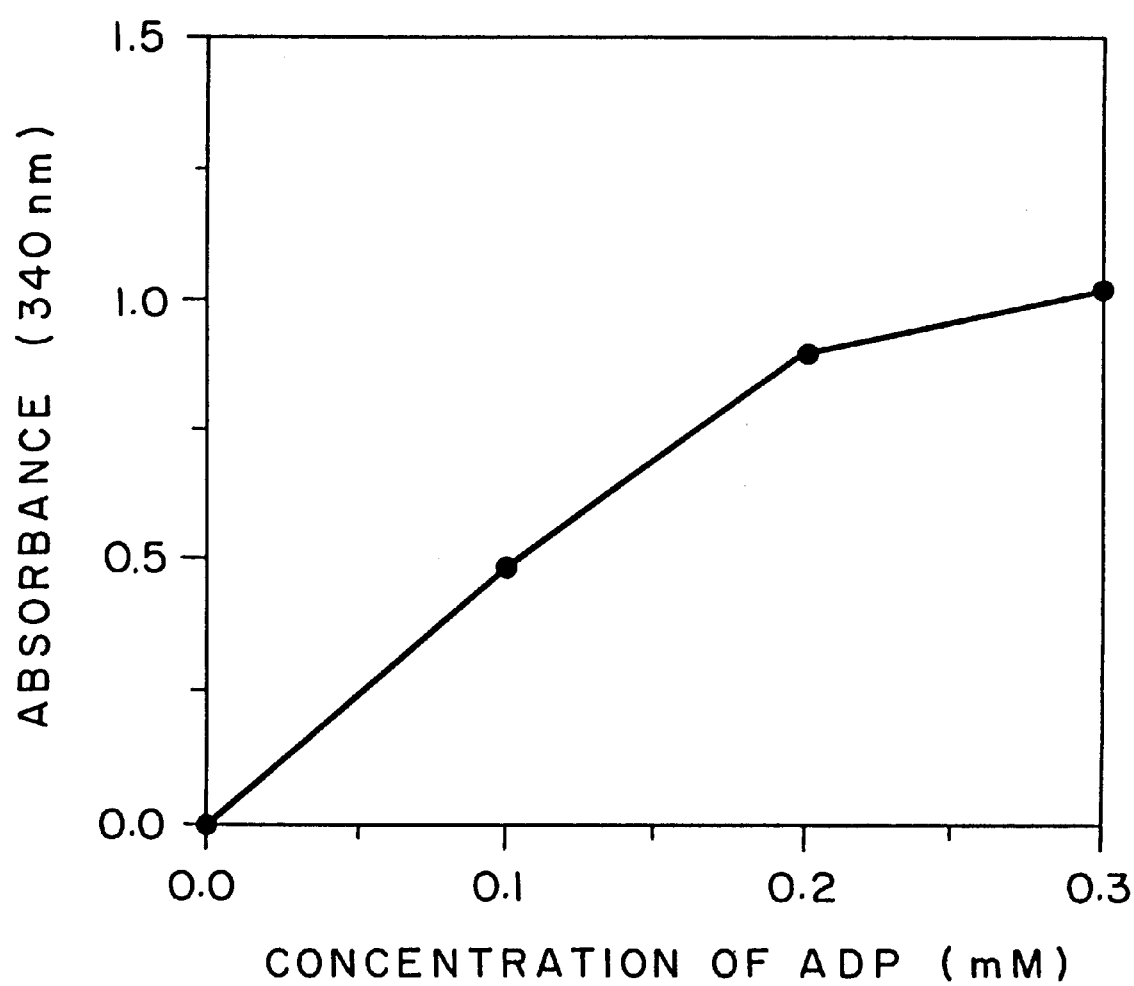
FIG. 17 Qualitative assay curve for assaying ADP at 50° C. in place of this invention.

ADO aqueous solution was prepared at concentration of 0.5 mM, 10 mM and 15 mM to prepare ADO sample. After the reagent for assay 1 ml was preheated at 50° C. for 5 minutes, ADO sample 20 μl was added therein, and the optical absorption at 340 nm was measured after incubation at 50° C. for 5 minutes with a control of the reagent blank solution. As shown in FIG. 17, ADP could not be assayed quantitatively.

Effect of the Invention

In the method of the present invention, since the biological sample is assayed based on the generated amount of reduced NAD(P), the assay limit is high. Since the reduced NAD(P), in which the molecular absorption coefficient is clearly defined, is assayed, reliability of assay data is high. Further, the assay method of the present invention has advantages without influence of the reducing active substance in the specimen. Consequently, according to the present invention, ADP in the biological sample or the enzyme, which generates ADP, and substrate thereof in the biological sample can be assayed with simply and precisely.

We claim:

1. A method for determining adenosine 5' diphosphate (ADP) contained in a liquid sample by means of an enzymatic reaction, which comprises reacting the sample at 15 to 45° C. at least in the presence of glucose, ADP-dependent hexokinase, oxidized NAD (P), glucose-6-phosphate dehydrogenase, and one or more ion releasing salts selected from the group consisting of magnesium, cobalt and manganese ions, and determining the ADP contained in the sample together with the AMP resulting from the reaction based on the amount of the reduced NAD (P) yielded.

2. The method according to claim 1 wherein ADP exists or is ADP generated in the sample.

3. The method according to claim 1 wherein ADP-dependent hexokinase is super thermophile ADP-dependent hexokinase.

4. The method according to claim 1 wherein temperature for reaction is 20–40° C.

5. The method according to claim 1 wherein concentration of ADP-dependent hexokinase and glucose-6-phosphate dehydrogenase is 0.1–100 U/ml; concentration of glucose is 0.5–100 mM; concentration of oxidized NAD(P) is 5–50 mM; and concentration of ion releasing salt is 0.1–50 mM.

6. A method for determining an enzyme for generating ADP or substrate thereof in a liquid sample by means of an enzymatic reaction, which comprises reacting the sample containing the enzyme for generating ADP or substrate thereof in the liquid sample at 15 to 45° C. at least in the presence of a reaction reagent involving in the reaction based on the enzyme for generating ADP and the substrate thereof, ATP, glucose, ADP-dependent hexokinase, oxidized NAD(P), glucose-6-phosphate dehydrogenase and one or more ion releasing salt of magnesium ion, cobalt ion or manganese ion, and determining the enzyme for generating ADP or the substrate thereof contained in the sample together with the AMP resulting from the reaction based on the amount of the reduced NAD (P) yielded.

7. The method according to claim 6 wherein the enzyme for generating ADP is urea amidohydrolase and the substrate thereof is urea.

8. The method according to claim 6 wherein the enzyme for generating ADP is creatine kinase and the substrate thereof is creatine.

9. The method according to claim 8 wherein creatine is the creatine liberated from creatinine by an action of creatinase.

10. The method according to claim 6 wherein the enzyme for generating ADP is N-methylhydantoinase and the substrate thereof is N-methylhydantoin.

11. The method according to claim 10 wherein N-methylhydantoin is the N-methylhydantoin liberated from creatinine by an action of creatinase deiminase.

12. The method according to claim 6 wherein the enzyme for generating ADP is glycerol kinase and the substrate thereof is glycerol.

13. The method according to claim 12 wherein glycerol is the glycerol liberated from triglyceride, diglyceride or monoglyceride by an action of lipase or the glycerol liberated from phosphatidylglycerol by an action of phospholipase D.

14. The method according to claim 6 wherein the enzyme for generating ADP is choline kinase and the substrate thereof is choline.

15. The method according to claim 14 wherein choline is the choline liberated from phosphatidylcholine by an action of phospholipase D or the choline liberated from choline ester by an action of choline esterase.

16. The method according to claim 6 wherein the enzyme for generating ADP is glutamine synthetase or glutamate kinase and the substrate thereof is L-glutamate.

17. The method according to claim 16 wherein L-glutamate is the L-glutamate liberated from L-aspartate and α-ketoglutarate by an action of aspartate aminotransferase.

18. The method according to claim 16 wherein L-glutamate is the L-glutamate liberated from L-alanine and α-ketoglutarate by an action of alanine aminotransferase.

19. The method according to claim 6 wherein ADP-dependent hexokinase is super thermophile ADP-dependent hexokinase.

20. The method according to claim 5 wherein temperature for reaction is 20–40° C.

* * * * *